(12) United States Patent
Aso et al.

(10) Patent No.: US 8,039,500 B2
(45) Date of Patent: Oct. 18, 2011

(54) FUSED HETEROCYCLIC COMPOUNDS

(75) Inventors: Kazuyoshi Aso, Osaka (JP); Michiyo Mochizuki, Osaka (JP); Katsumi Kobayashi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/448,271

(22) PCT Filed: Dec. 28, 2007

(86) PCT No.: PCT/JP2007/075427
§ 371 (c)(1),
(2), (4) Date: Jun. 16, 2009

(87) PCT Pub. No.: WO2008/082003
PCT Pub. Date: Jul. 10, 2008

(65) Prior Publication Data
US 2010/0048658 A1  Feb. 25, 2010

Related U.S. Application Data

(60) Provisional application No. 60/877,628, filed on Dec. 29, 2006.

(51) Int. Cl.
*A61K 31/4184* (2006.01)
*C07D 235/14* (2006.01)
(52) U.S. Cl. ............ 514/395; 514/394; 548/307.4
(58) Field of Classification Search .......... 514/394, 514/395; 548/307.4
See application file for complete search history.

(56) References Cited

U.S. PATENT DOCUMENTS
2006/0160872 A1  7/2006  Norman et al.

FOREIGN PATENT DOCUMENTS

| EP | 0 178 413 | 4/1986 |
|---|---|---|
| WO | 96/11917 | 4/1996 |
| WO | 97/48697 | 12/1997 |
| WO | 98/05327 | 2/1998 |
| WO | 98/38188 | 9/1998 |
| WO | 03/037860 | 5/2003 |
| WO | 2005/044793 | 5/2005 |
| WO | 2005/060958 | 7/2005 |
| WO | 2005/099688 | 10/2005 |
| WO | 2006/062972 | 6/2006 |
| WO | 2006/099379 | 9/2006 |
| WO | 2006/116412 | 11/2006 |
| WO | 2007/017794 | 2/2007 |
| WO | 2008/051533 | 5/2008 |

OTHER PUBLICATIONS

STN_12448271_09282010.*
Deng et al., Bioorg. Med. Chem. Lett., vol. 15, (2005), p. 4411-16.*
International Search Report issued Jun. 12, 2008 in International (PCT) Application No. PCT/JP2007/075427.
D. J. Sall et al., "Inhibition of Phenylethanolamine N-Methyltransferase (PNMT) by Aromatic Hydroxy-Substituted 1,2,3,4-Tetrahydroisoquinolines: Further Studies on the Hydrophilic Pocket of the Aromatic Ring Binding Region of the Active Site", J. Med. Chem., vol. 30, pp. 2208-2216, 1987.
D. Sperandio et al., "Highly Potent Non-Peptide Inhibitors of the HCV NS3/NS4A Serine Protease", Bioorganic & Medicinal Chemistry Letters, vol. 12, pp. 3129-3133, 2002.
S. P. Gupta et al., "Quantitative Structure-Activity Relationship Study on Some 5-Lipoxygenase Inhibitors", J. Enzyme Inhibition, vol. 3, pp. 179-188, 1990.
R. Chen et al., "Expression cloning of a human corticotropin-releasing-factor receptor", Proc. Natl. Acad. Sci., vol. 90, pp. 8967-8971, Oct. 1993.

* cited by examiner

*Primary Examiner* — Yong Chu
(74) *Attorney, Agent, or Firm* — Wenderoth, Lind & Ponack, L.L.P.

(57) ABSTRACT

There is provided a compound of the formula:

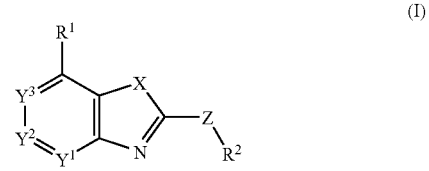

(I)

wherein $R^1$ is an optionally substituted hydrocarbyl, a substituted amino, etc.; $R^2$ is an aromatic group substituted with one or two substituents at the positions adjacent to the position bonded to Z, and said aromatic group may have additional substituent(s); X is —$NR^3$— wherein $R^3$ is a hydrogen, an optionally substituted hydrocarbyl or an acyl, or sulfur; $Y^1$, $Y^2$ and $Y^3$ are an optionally substituted methine or a nitrogen, etc.; and Z is an optionally substituted methylene, provided that carbonyl is excluded; or a salt thereof or a prodrug thereof, which have CRF receptor antagonist activity and use thereof.

10 Claims, No Drawings

FUSED HETEROCYCLIC COMPOUNDS

This application is a U.S. national stage of International Application No. PCT/JP2007/075427 filed Dec. 28, 2007, which claims the benefit of U.S. provisional application Ser. No. 60/877,628 filed Dec. 29, 2006.

TECHNICAL FIELD

The present invention relates to novel fused heterocyclic compounds having corticotropin-releasing factor antagonistic activity and pharmaceutical compositions containing them.

BACKGROUND OF INVENTION

Corticotropin-releasing factor (hereinafter, abbreviated as "CRF") is a neuropeptide composed of 41 amino acids, and was isolated and purified as a peptide promoting release of adrenocorticotropic hormone (ACTH) from pituitary gland. First, the structure thereof was determined from sheep hypothalamus and, thereafter, the presence thereof was confirmed also in a rat or a human, and the structure thereof was determined [Science, 213, 1394 (1981); Proc. Natl. Acad. Sci. USA, 80, 4851 (1983); EMBO J. 5, 775 (1983)]. An amino acid sequence is the same in a human and a rat, but differed in 7 amino acids in ovine. CRF is synthesized as a carboxy-terminal of prepro CRF, cut and secreted. The CRF peptide and an mRNA thereof are present at the largest amount in hypothalamus and pituitary gland, and are widely distributed in a brain such as cerebral cortex, cerebellum, hippocampus and corpus amygdaloideum. In addition, in peripheral tissues, the existence has been confirmed in placenta, adrenal gland, lung, liver, pancreas, skin and digestive tract [J. Clin. Endocrinol. Metab., 65, 176 (1987); J. Clin. Endocrinol. Metab., 67, 768 (1988); Regul. Pept., 18, 173 (1987), Peptides, 5 (Suppl. 1), 71 (1984)]. A CRF receptor is a 7-transmembrane G protein-coupled receptor, and two subtypes of CRF1 and CRF2 are present. It is reported that CRF1 is present mainly in cerebral cortex, cerebellum, olfactory bulb, pituitary gland and tonsil nucleus. On the other hand, the CRF2 receptor has two subtypes of CRF2$\alpha$ and CRF2$\beta$. It was made clear that the CRF2$\alpha$ receptor is distributed much in hypothalamus, septal area and choroids plexus, and the CRF2$\beta$ receptor is present mainly in peripheral tissues such as skeletal muscle and is distributed in a blood vessel in a brain [J. Neurosci. 15, 6340 (1995); Endocrinology, 137, 72 (1996); Biochim. Biophys. Acta, 1352, 129 (1997)]. Since each receptor differs in distribution in a living body, it is suggested that a role thereof is also different [Trends. Pharmacol. Sci. 23, 71 (2002)].

As a physiological action of CRF, the action on the endocrine system is known in which CRF is produced and secreted in response to stress in hypothalamus and acts on pituitary gland to promote the release of ACTH [Recent Prog. Horm. Res., 39, 245 (1983)]. In addition to the action on the endocrine system, CRF acts as a neurotransmitter or a neuroregulating factor in a brain, and integrates electrophysiology, autonomic nerve and conducts to stress [Brain Res. Rev., 15, 71 (1990); Pharmacol. Rev., 43, 425 (1991)]. When CRF is administered in a cerebral ventricle of experimental animal such as a rat, anxiety conduct is observed, and much more anxiety conduct is observed in a CRF-overexpressing mouse as compared with a normal animal [Brain Res., 574, 70 (1992); J. Neurosci., 10, 176 (1992); J. Neurosci., 14, 2579 (1994)]. In addition, $\alpha$-helical CRF (9-41) of a peptidergic CRF receptor antagonist exerts an anxiolytic action in an animal model [Brain Res., 509, 80 (1990); J. Neurosci., 14, 2579 (1994)]. A blood pressure, a heart rate and a body temperature of a rat are increased by stress or CRF administration, but the $\alpha$-helical CRF (9-41) of a peptidergic CRF antagonist inhibits the increase in a blood pressure, a heart rate and a body temperature due to stress [J. Physiol., 460, 221 (1993)]. The $\alpha$-helical CRF (9-41) of a peptidergic CRF receptor antagonist inhibits abnormal conducts due to withdrawal of a dependent drug such as an alcohol and a cocaine [Psychopharmacology, 103, 227 (1991); Pharmacol. Rev. 53, 209 (2001)]. In addition, it has been reported that learning and memory are promoted by CRF administration in a rat [Nature, 375, 2.84 (1995); Neuroendocrinology, 57, 1071 (1993); Eur. J. Pharmacol., 405, 225 (2000)].

Since CRF is associated with stress response in a living body, there are clinical reports regarding stress-associated depression or anxiety. The CRF concentration in a cerebrospinal fluid of a depression patient is higher as compared with that of a normal person [Am. J. Psychiatry, 144, 873 (1987)], and the mRNA level of CRF in hypothalamus of a depression patient is increased as compared with that of a normal person [Am. J. Psychiatry, 152, 1372 (1995)]. A CRF binding site of cerebral cortex of a patient who suicided by depression is decreased [Arch. Gen. Psychiatry, 45, 577 (1988)]. The increase in the plasma ACTH concentration due to CRF administration is small in a depression patient [N. Engl. J. Med., 314, 1329 (1986)]. In a patient with panic disorder, the increase of plasma ACTH concentration due to CRF administration is small [Am. J. Psychiatry, 143, 896 (1986)]. The CRF concentration in a cerebrospinal fluid of a patient with anxiety induced by stress such as obsessive-compulsive neurosis, post-psychic trauma stress disorder, Tourette's syndrome and the like is higher as compared with that of a normal person [Arch. Gen. Psychiatry, 51, 794 (1994); Am. J. Psychiatry, 154, 624 (1997); Biol. Psychiatry, 39, 776 (1996)]. The CRF concentration in a cerebrospinal fluid of schizophrenics is higher as compared with that of a normal person [Brain Res., 437, 355 (1987); Neurology, 37, 905 (1987)]. Thus, it has been reported that there is abnormality in the living body response system via CRF in stress-associated mental disease.

The action of CRF on the endocrine system can be presumed by the characteristics of CRF gene-introduced animal and actions in an experimental animal. In a CRF-overexpressing mouse, excessive secretions of ACTH and adrenal cortex steroid occur, and abnormalities analogous to Cushing's syndrome such as atrophy of muscle, alopecia, infertility and the like are observed [Endocrinology, 130, 3378 (1992)]. CRF inhibits ingestion in an experimental animal such as a rat [Life Sci., 31, 363 (1982); Neurophamacology, 22, 337 (1983)]. In addition, $\alpha$-helical CRF (9-41) of a peptidergic CRF antagonist inhibited decrease of ingestion due to stress loading in an experimental model [Brain Res. Bull., 17, 285 (1986)]. CRF inhibited weight gain in a hereditary obesity animal [Physiol. Behav., 45, 565 (1989)]. In a nervous orexia inactivity patient, the increase of ACTH in plasma upon CRF administration is small [J. Clin. Endocrinol. Metab., 62, 319 (1986)]. It has been suggested that a low CRF value is associated with obesity syndrome [Endocrinology, 130, 1931 (1992)]. There has been suggested a possibility that ingestion inhibition and weight loss action of a serotonin reuptake inhibiting agent are exerted via release of CRF [Pharmacol. Rev., 43, 425 (1991)].

CRF is centrally or peripherally associated with the digestive tract movement involved in stress or inflammation [Am. J. Physiol. Gastrointest. Liver Physiol. 280, G315 (2001)]. CRF acts centrally or peripherally, weakens the shrinkablity of stomach, and decreases the gastric excreting ability [Regulatory Peptides, 21, 173 (1988); Am. J. Physiol., 253, G241

(1987)]. In addition, α-helical CRF (9-41) of a peptidergic CRF antagonist has a restoring action for hypofunction of stomach by abdominal operation [Am. J. Physiol., 258, G152 (1990)]. CRF inhibits secretion of a bicarbonate ion in stomach, decreases gastric acid secretion and inhibits ulcer due to cold restriction stress [Am. J. Physiol., 258, G152 (1990)]. Furthermore, α-helical CRF (9-41) of a peptidergic CRF antagonist shows the inhibitory action on gastric acid secretion decrease, gastric excretion decrease, small intestinal transport decrease and large intestinal transport enhancement due to restriction stress [Gastroenterology, 95, 1510 (1988)]. In a healthy person, mental stress increases a gas and abdominal pain due to anxiety and intestine dilation, and CRF decreases a threshold of discomfort [Gastroenterology, 109, 1772 (1995); Neurogastroenterol. Mot., 8, 9-[1996]. In an irritable bowel syndrome patient, large intestinal movement is excessively enhanced by CRF administration as compared with a healthy person [Gut, 42, 845 (1998)].

It has been reported from studies on experimental animals and clinical studies that CRF is induced by inflammation and is involved in an inflammatory reaction. In an inflammatory site of an experimental animal and in a joint fluid of a rheumatoid arthritis patient, production of CRF is topically increased [Science, 254, 421 (1991); J. Clin. Invest., 90, 2555 (1992); J. Immunol., 151, 1587 (1993)]. CRF induces degranulation of a mast cell and enhances the blood vessel permeability [Endocrinology, 139, 403 (1998); J. Pharmacol. Exp. Ther., 288, 1349 (1999)]. CRF can be detected also in a thyroid gland of autoimmune thyroiditis patient [Am. J. Pathol. 145, 1159 (1994)]. When CRF is administered to an experimental autoimmune cerebrospinal meningitis rat, the progression of symptom such as paralysis was remarkably inhibited [J. Immunil., 158, 5751 (1997)]. In a rat, the immune response activities such as T-lymphocyte proliferation and the natural killer cell activity are reduced by CRF administration or stress loading [Endocrinology, 128, 1329 (1991)].

From the above-mentioned reports, it is expected that the CRF receptor antagonistic compound would exert an excellent effect for treating or preventing various diseases in which CRF is associated.

As a CRF antagonist, for example, peptide CRF receptor antagonists are reported in which a part of an amino acid sequence of CRF or associated peptides of a human or other mammals is altered or deleted, and they are reported to show a pharmacological action such as ACTH release-inhibiting action and anti-anxiety action [Science, 224, 889 (1984); J. Pharmacol. Exp. Ther., 269, 564 (1994); Brain Res. Rev., 15, 71 (1990)]. However, from a pharmacokinetic point of view such as chemical stability and absorbability for oral administration in a living body, bioavailability and intracerebral transferability, peptide derivatives have a low utility value as a medicine.

As a CRF antagonistic compound, for example, nitrogen-containing fused heterocyclic compounds are reported in WO 2005/44793, WO2005/099688 and WO 2006/116412.

WO 97/48697, WO 98/5327, J. Med. Chem., 30, 2216 (1987), WO 2005/060958, WO 98/38188, WO 2006/062972, and WO 2006/099379 disclose benzimidazole compounds.

DISCLOSURE OF INVENTION

According to the present invention, there is provided:
1) A compound represented by the formula (I):

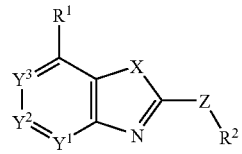

wherein $R^1$ is (1) an optionally substituted hydrocarbyl, (2) an amino substituted with one or two substituents selected from an optionally substituted hydrocarbyl and an optionally substituted heterocyclic group, (3) an optionally substituted cyclic amino, (4) an optionally substituted heterocyclic group, (5) an acyl, or (6) an optionally substituted hydrocarbyloxy;

$R^2$ is an aromatic group substituted with one or two substituents at the positions adjacent to the position bonded to Z, and said aromatic group may have additional substituent(s);

X is (1) —$NR^3$— wherein $R^3$ is a hydrogen, an optionally substituted hydrocarbyl or an acyl, or (2) sulfur;

$Y^1$, $Y^2$ and $Y^3$ are each an optionally substituted methine or a nitrogen, provided that one or less of $Y^1$, $Y^2$ and $Y^3$ is nitrogen; and Z is an optionally substituted methylene, provided that carbonyl is excluded;

provided that (1) N-(3,5-dichloro-4-pyridyl)-7-methoxy-2-(2-methoxybenzyl)-3H-benzimidazole-4-carboxamide,
(2) 1'-benzotriazolyl 7-methoxy-2-(2-methoxybenzyl)-3H-benzimidazole-4-carboxylate,
(3) 7-methoxy-2-(2-methoxybenzyl)-3H-benzimidazole-4-carboxylic acid,
(4) methyl 7-methoxy-2-(2-methoxybenzyl)-3H-benzimidazole-4-carboxylate,
(5) 6-benzyloxy-2-(7-methoxy-2-(2-methoxybenzyl)-3H-benzimidazol-4-yl)-2-pyrid-4-ylmethylindan-1,3-dione,
(6) 3-(7-methoxy-2-(2-methoxybenzyl)-3H-benzimidazol-4-yl)-pyrrolidine-2-one-1-carboxylic acid tert-butyl ester,
(7) 6-benzyloxy-2-(7-methoxy-2-(2-methoxybenzyl)-3H-benzimidazol-4-yl)indan-1,3-dione,
(8) 7-methoxy-2-(2-methoxybenzyl)-3H-benzimidazol-4-ylacetic acid,
(9) 7-methoxy-2-(2-methoxybenzyl)-3H-benzimidazole-4-carboxylic acid chloride,
(10). 7-methoxy-2-(2-methoxybenzyl)-3H-benzimidazole-4-carboxylic acid,
(11) methyl 7-methoxy-2-(2-methoxybenzyl)-3H-benzimidazole-4-carboxylate,
(12) methyl 3-cyano-2-(7-methoxy-2-(2-methoxybenzyl)-3H-benzimidazol-4-yl)propanoate,
(13) 3-(7-methoxy-2-(2-methoxybenzyl)-3H-benzimidazol-4-yl)-pyrrolidine-2-one,
(14) 4-benzyloxy-2-(2-methoxybenzyl)-7-methyl-1H-benzimidazole,
(15) 4-hydroxy-2-(2-methoxybenzyl)-7-methyl-1H-benzimidazole,
(16) 2-(4-methyl-2-(4-(trifluoromethyl)phenyl)thiazol-5-yl)methylbenzothiazol-7-ylacetic acid,
(17) 2-(4-methyl-2-(4-(trifluoromethyl)phenyl)thiazol-5-yl)methylbenzothiazol-7-yloxyacetic acid,
(18) 2-methyl-2-(2-(4-methyl-2-(4-(trifluoromethyl)phenyl)thiazol-5-yl)methylbenzothiazol-7-yloxy)propanoic acid,
(19) 3-[4-chloro-2-[(2-chlorophenyl)methyl]-6-fluoro-1H-benzimidazol-7-yl]-1-methyl-6-(trifluoromethyl)-2,4(1H,3H)-pyrimidinedione,

(20) 4-((5-ethoxy-2-fluoro-3-isopropoxyphenyl)(4-methyl-1H-benzo[d]imidazol-2-yl)methylamino)benzamidine,
(21) 4-((5-ethoxy-2-fluoro-3-isopropoxyphenyl)(4-methoxy-1H-benzo[d]imidazol-2-yl)methylamino)benzamidine,
(22) 4-((4,5-dimethyl-1H-benzo[d]imidazol-2-yl)(5-ethoxy-2-fluoro-3-isopropoxyphenyl)methylamino)benzamidine,
(23) 4-((4,6-dimethyl-1H-benzo[d]imidazol-2-yl)(5-ethoxy-2-fluoro-3-isopropoxyphenyl)methylamino)benzamidine,
(24) N-[[1-methyl-2-[(4-methyl-1H-benzimidazol-2-yl)methyl]-1H-benzimidazol-6-yl]carbonyl]-3-phosphonoalanine,
(25) N-[[2-[(4-methoxy-1H-benzimidazol-2-yl)methyl]-1-methyl-1H-benzimidazol-6-yl]carbonyl]-3-phosphonoalanine,
(26) N-[[2-[difluoro(4-methyl-1H-benzimidazol-2-yl)methyl]-1-methyl-1H-benzimidazol-6-yl]carbonyl]-3-phosphonoalanine, and
(27) 2-[(methoxyphenyl)methyl]-7-methyl-1H-benzimidazol-4-ol are excluded;

or a salt thereof (hereinafter, sometimes abbreviated as "Compound (I)");

2) A prodrug of the compound according to the above-mentioned 1);
3) The compound according to the above-mentioned 1) wherein $R^2$ is an optionally substituted $C_{3-10}$ alkyl, an optionally substituted $C_{3-10}$ alkenyl or an amino substituted with two optionally substituted $C_{1-4}$ alkyls;
4) The compound according to the above-mentioned 1) wherein $R^2$ is (i) 2,4,6-trisubstituted phenyl, (ii) 2,4-disubstituted phenyl, (iii) 2,4,6-trisubstituted 3-pyridyl, (iv) 2,6- or 4,6-disubstituted 3-pyridyl, or (v) 3,5-disubstituted 2-pyridyl;
5) The compound according to the above-mentioned 1) wherein X is —$NR^3$—;
6) The compound according to the above-mentioned 1) wherein $Y^1$, $Y^2$ and $Y^3$ are methines;
7) The compound according to the above-mentioned 1) wherein Z is a methylene or a hydroxymethylene;
8) The compound according to the above-mentioned 1) wherein $R^1$ is (1) $C_{3-10}$ alkyl optionally substituted with hydroxy or $C_{1-6}$ alkyl-carbonyloxy, (2) $C_{3-10}$ alkenyl or (3) di-$C_{1-4}$ alkylamino;

$R^2$ is 2,4,6-trisubstituted phenyl, wherein the substituent is selected from the group consisting of (1) halogen atom and (2) optionally halogenated $C_{1-4}$ alkyl;
X is —N($C_{1-6}$ alkyl)-;
$Y^1$ is CH;
$Y^2$ is CH;
$Y^3$ is CH; and
Z is a methylene or a hydroxymethylene;

9) (1) N,N-diethyl-2-(mesitylmethyl)-1-methyl-1H-benzimidazol-7-amine;
(2) 2-[2,6-dichloro-4-(trifluoromethyl)benzyl]-N,N-diethyl-1-methyl-1H-benzimidazol-7-amine;
(3) 3-[2-(mesitylmethyl)-1-methyl-1H-benzimidazol-7-yl]pentan-3-ol;
(4) 7-[1-ethylprop-1-en-1-yl]-2-(mesitylmethyl)-1-methyl-1H-benzimidazole;
(5) 7-(1-ethylpropyl)-2-(mesitylmethyl)-1-methyl-1H-benzimidazole;
(6) 3-{2-[2,6-dichloro-4-(trifluoromethyl)benzyl]-1-methyl-1H-benzimidazol-7-yl}pentan-3-ol;
(7) 2-[2,6-dichloro-4-(trifluoromethyl)benzyl]-7-[1-ethylprop-1-en-1-yl]-1-methyl-1H-benzimidazole;
(8) 2-{2-[2,6-dichloro-4-(trifluoromethyl)benzyl]-1-methyl-1H-benzimidazol-7-yl}-1-methylbutyl acetate;
(9) 3-{2-[2,6-dichloro-4-(trifluoromethyl)benzyl]-1-methyl-1H-benzimidazol-7-yl}pentan-2-ol; or
(10) [7-(1-ethylpropyl)-1-methyl-1H-benzimidazol-2-yl](mesityl)methanol; or a salt thereof;

10) A pharmaceutical which comprises the compound according to the above-mentioned 1) or its prodrug;
11) The pharmaceutical according to the above-mentioned 10) which is for treating or preventing a disease associated with the functions of a CRF receptor;
12) The pharmaceutical according to the above-mentioned 11) wherein the disease is affective disorder, depression or anxiety;
13) A method for treating or preventing a disease associated with the functions of a CRF receptor, which comprises administering to a subject in need thereof an effective amount of the compound according to the above-mentioned 1) or its prodrug;
14) The method according to the above-mentioned 13) wherein the disease is affective disorder, depression or anxiety;
15) Use of the compound according to the above-mentioned 1) or its prodrug for manufacturing an agent of treating or preventing a disease associated with the functions of a CRF receptor;
16) The use according to the above-mentioned 15) wherein the disease is affective disorder, depression or anxiety; and the like.

Each symbol in the above formulae is hereinafter described in more detail.

In this specification, the "hydrocarbyl" of "an optionally substituted hydrocarbyl" includes, for example, an aliphatic hydrocarbon group, an alicyclic hydrocarbon group, an alicyclic-aliphatic hydrocarbon group, an aromatic hydrocarbon group, an aromatic-aliphatic hydrocarbon group (an aralkyl), and the like.

Examples of the "aliphatic hydrocarbon group" described above include a $C_{1-8}$ alkyl (e.g., methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.), a $C_{2-8}$ alkenyl (e.g., vinyl, allyl, 1-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 1-heptenyl, 1-octenyl, etc.), a $C_{2-8}$ alkynyl (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, etc.), a $C_{2-8}$ alkadienyl (e.g., 2,4-hexadienyl, etc.), a $C_{2-8}$ alkadiynyl (e.g., 2,4-hexadiynyl, etc.), etc.

Examples of the "alicyclic hydrocarbon group" described above include a $C_{3-7}$ cycloalkyl (e.g., cyclopropyl, cyclobutyl, cyclopentyl, cyclohexyl, cycloheptyl, etc.), a $C_{3-7}$ cycloalkenyl (e.g., 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, etc.), a $C_{3-7}$ cycloalkadienyl (e.g., 2,4-cycloheptadienyl, etc.), a partly saturated and fused bicyclic hydrocarbon group, preferably, $C_{9-10}$ partly saturated and fused bicyclic hydrocarbon group, etc. (including those where the benzene ring is combined to 5- or 6-membered non-aromatic cyclic hydrocarbon group) such as 1-indenyl, 2-indenyl, 1-indanyl, 2-indanyl, 1,2,3,4-tetrahydro-1-naphthyl, 1,2,3,4-tetrahydro-2-naphthyl, 1,2-dihydro-1-naphthyl, 1,2-dihydro-2-naphthyl, 1,4-dihydro-1-naphthyl, 1,4-dihydro-2-naphthyl, 3,4-dihydro-1-naphthyl, 3,4-dihydro-2-naphthyl, etc., and the like. Said alicyclic hydrocarbon group may be cross-linked.

Examples of the "alicyclic-aliphatic hydrocarbon group" described above include those where the above-mentioned alicyclic hydrocarbon group and the above-mentioned aliphatic hydrocarbon group are combined, for example, a $C_{3-7}$ cycloalkyl-$C_{1-4}$ alkyl, a $C_{3-7}$ cycloalkenyl-$C_{1-4}$ alkyl, a $C_{3-7}$ cycloalkyl-$C_{2-4}$ alkenyl, a $C_{3-7}$ cycloalkenyl-$C_{2-4}$ alkenyl, a $C_{9-10}$ partly saturated and fused bicyclic hydrocarbon-$C_{1-4}$ alkyl, or a $C_{9-10}$ partly saturated and fused bicyclic hydrocarbon-$C_{2-4}$ alkenyl (e.g., cyclopropylmethyl, cyclopropylethyl, cyclobutylmethyl, cyclobutylethyl, cyclopentylmethyl, 2-cyclopentenylmethyl, 3-cyclopentenylmethyl, cyclopentylethyl, cyclohexylmethyl, 2-cyclohexenylmethyl, 3-cyclohexenylmethyl, cyclohexylethyl, cycloheptylmethyl, cycloheptylethyl, 2-(3,4-dihydro-2-naphtyl)ethyl, 2-(1,2,3,4-tetrahydro-2-naphtyl)ethyl, 2-(3,4-dihydro-2-naphtyl)ethenyl, etc.), and the like.

Examples of the "aromatic hydrocarbon group" described above include a $C_{6-10}$ aryl (including that where a 5- to 6-membered non-aromatic hydrocarbon ring is fused with phenyl) such as phenyl, α-naphthyl, β-naphthyl, 4-indenyl, 5-indenyl, 4-indanyl, 5-indanyl, 5,6,7,8-tetrahydro-1-naphthyl, 5,6,7,8-tetrahydro-2-naphthyl, 5,6-dihydro-1-naphthyl, 5,6-dihydro-2-naphthyl, 5,6-dihydro-3-naphthyl, 5,6-dihydro-4-naphthyl, and the like.

Examples of the "aromatic-aliphatic hydrocarbon group" described above include a $C_{7-14}$ aralkyl, etc. Examples of the $C_{7-14}$ aralkyl include a $C_{6-10}$ aryl-$C_{1-4}$ alkyl such as a phenyl-$C_{1-4}$ alkyl (e.g., benzyl, phenethyl, 1-phenylethyl, 1-phenylpropyl, 2-phenylpropyl, 3-phenylpropyl, etc.), a naphthyl-$C_{1-4}$ alkyl (e.g., α-naphthylmethyl, α-naphthylethyl, β-naphthylmethyl, β-naphthylethyl, etc.), a $C_{6-10}$ aryl-$C_{2-4}$ alkenyl (e.g., phenyl-$C_{2-4}$ alkenyl such as styryl, cinnamyl, etc.), and the like.

The substituents of the "optionally substituted hydrocarbyl" include, for example, amino, mono- or di-$C_{1-6}$ alkylamino (e.g., mono-$C_{1-6}$ alkylamino such as methylamino, ethylamino, propylamino, isopropylamino, butylamino. etc; di-$C_{1-6}$ alkylamino such as dimethylamino, diethylamino, ethylmethylamino, dipropylamino, diisopropylamino, dibutylamino, etc.), halogen atom (e.g., fluoro, chloro, bromo, iodo), nitro, cyano, optionally halogenated $C_{1-6}$ alkyl (e.g., methyl, ethyl, propyl, isopropyl, butyl, isobutyl, tert-butyl, trifluoromethyl, etc.), $C_{1-6}$ alkoxy-$C_{1-6}$ alkyl (e.g., methoxyethyl, ethoxymethyl, etc.), amino-$C_{1-6}$ alkyl. (e.g., aminomethyl, etc.), mono- or di-$C_{1-6}$ alkylamino-$C_{1-6}$ alkyl (e.g., methylaminomethyl, dimethylaminoethyl, etc.), $C_{2-6}$ alkenyl (e.g., vinyl, allyl, propenyl, etc.), $C_{2-6}$ alkynyl (e.g., ethynyl, etc.), $C_{3-7}$ cycloalkyl (e.g., cyclopropyl, cyclobutyl, cyclopentyl, cyclohexyl, etc.), $C_{6-14}$ aryl (e.g., phenyl, 1-naphthyl, 2-naphthyl, 2-biphenyl, 3-biphenyl, 4-biphenyl, etc.), $C_{7-19}$ aralkyl (e.g., benzyl, etc.), 5- or 6-membered aromatic heterocyclic group (e.g., furyl, thienyl, 1- or 3-pyrrolyl, 2-oxazolyl, 3-isoxazolyl, thiazolyl, 3-isothiazolyl, 1- or 2-imidazolyl, 1-pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, 2-, 3- or 4-pyridyl, 2- or 4-pyrimidinyl, 3-pyridazinyl, pyrazinyl, triazinyl, etc.). 3- to 6-membered non-aromatic heterocyclic group (e.g., oxiranyl, azetidinyl, oxetanyl, thietanyl, 1-, 2- or 3-pyrrolidinyl, tetrahydrofuryl, thiolanyl, piperidinyl, tetrahydropyranyl, morpholinyl, thiomorpholinyl, piperazinyl, etc.), 8- to 12-membered bicyclic or tricyclic fused heterocyclic group (e.g., benzofuranyl, isobenzofuranyl, benzothienyl, indolyl, isoindolyl, 1H-indazolyl, benzindazolyl, benzoxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, 1,2,5,6-tetrahydro-4H-pyrrolo[3,2,1-ij]quinolinyl, etc.), optionally halogenated $C_{1-6}$ alkoxy (e.g., methoxy, ethoxy, propoxy, tert-butoxy, trifluoromethoxy, etc.), hydroxy, $C_{6-14}$ aryloxy (e.g., phenyloxy, 1-naphthyloxy, etc.), $C_{7-16}$ aralkyloxy (e.g., benzyloxy, phenetyloxy, etc.), hydroxyamino, mono-$C_{6-14}$ arylamino (e.g., phenylamino, 1-naphthylamino, etc.), di-$C_{6-14}$ arylamino (e.g., diphenylamino, etc.), $C_{1-6}$ alkyl-carbonylamino (e.g., acetylamino, propionylamino, etc.), $C_{1-6}$ alkoxy-carbonylamino (e.g., methoxycarbonylamino, ethoxycarbonylamino, etc.), 5- to 7-membered saturated cyclic amino (e.g., pyrrolidin-1-yl, piperidino, piperazin-1-yl, morpholino, thiomorpholino, homo piperazin-1-yl, etc.), formyl, carboxy, $C_{1-6}$ alkyl-carbonyl (e.g., acetyl, propionyl, etc.), $C_{3-6}$ cycloalkyl-carbonyl (e.g., cyclopropylcarbonyl, cyclobutylcarbonyl, cyclopentylcarbonyl, cyclohexylcarbonyl, etc.), $C_{1-6}$ alkoxy-carbonyl (e.g., methoxycarbonyl, ethoxycarbonyl, etc.), $C_{6-14}$ aryl-carbonyl (e.g., benzoyl, etc.), $C_{7-16}$ aralkyl-carbonyl (e.g., phenylacetyl, 3-phenylpropionyl, etc.), $C_{6-14}$ aryloxy-carbonyl (e.g., phenoxycarbonyl, etc.), $C_{7-16}$ aralkyloxy-carbonyl (e.g., benzyloxycarbonyl, etc.), 5- or 6-membered heterocyclic-carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-14}$ arylcarbamoyl (e.g., phenylcarbamoyl, 1-naphthylcarbamoyl, etc.), $C_{1-6}$ alkoxy-carbamoyl (e.g., methoxycarbamoyl, ethoxycarbamoyl, etc.), 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), mercapto, sulfo, $C_{1-6}$ alkylsulfinyl (e.g., methylsulfinyl, ethylsulfinyl, propylsulfinyl, butylsulfinyl etc.), $C_{6-14}$ arylsulfinyl (e.g., phenylsulfinyl, etc.), $C_{1-6}$ alkylsulfonyl (e.g., methylsulfonyl, ethylsulfonyl, propylsulfoyl, butylsulfonyl, etc.), $C_{6-14}$ arylsulfinyl (e.g., phenylsulfinyl, etc.), formylamino, $C_{1-6}$ alkyl-carbonylamino (e.g., acetylamino, etc.), $C_{6-14}$ aryl-carbonylamino (e.g., benzoylamino, etc.), $C_{1-6}$ alkoxy-carbonylamino (e.g., methoxycarbonylamino, ethoxycarbonylamino, etc.), $C_{1-6}$ alkylsulfinylamino (e.g., methylsulfinylamino, ethylsulfinylamino, propylsulfinylamino, butylsulfinylamino etc.), $C_{1-6}$ alkylsulfonylamino (e.g., methylsulfonylamino, ethylsulfonylamino, propylsulfoylamino, butylsulfonylamino, etc.), $C_{1-6}$ alkyl-carbonyloxy (e.g., acetoxy, propionyloxy, etc.), $C_{6-14}$ aryl-carbonyloxy (e.g., benzoyloxy, etc.), $C_{1-6}$ alkoxy-carbonyloxy (e.g., methoxycarbonyloxy, ethoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), $C_{6-14}$ aryl-carbamoyloxy (e.g., phenylcarbamoyloxy, etc.), 5- or 6-membered heterocyclic-carbonyloxy (e.g., nicotinoyloxy, isonicotinoyloxy, etc.), oxo, imino, $C_{1-6}$ alkylimino (e.g., methylimino, ethylimino, etc.), and the like. Among others, preferred substituents of the "optionally substituted hydrocarbyl" are amino, mono-$C_{1-6}$ alkylamino, di-$C_{1-6}$ alkylamino, halogen atom, optionally halogenated $C_{1-4}$ alkyl, 5- or 6-membered aromatic heterocyclic group, cyano, $C_{6-14}$ aryl, $C_{1-6}$ alkoxy, hydroxy, $C_{1-6}$ alkyl-carbonyloxy, oxo, and the like. More preferred substituents are halogen atom, halogenated $C_{1-4}$ alkyl, hydroxy, $C_{1-6}$ alkyl-carbonyloxy, and the like.

The "hydrocarbyl" may have 1 to 5, preferably 1 to 3, substituent(s) as mentioned above at possible positions and, when the number of substituents is two or more, those substituents may be the same as or different from one another.

In this specification, the "heterocyclic group" of "an optionally substituted heterocyclic group" includes, for example, a monovalent group produced by removing any one of hydrogen atoms from 5- to 14-membered (monocyclic, bicyclic or tricyclic) heterocycle containing 1 to 4 heteroatom(s) selected from 1 or 2 kind(s) of atoms which are nitrogen atom, sulfur atom and oxygen atom in addition to carbon atom(s), and the like. Preferable examples are monovalent groups produced by removing any one of hydrogen atoms from (i) 5- to 14-membered (preferably 5- to 10-membered) aromatic heterocycle, (ii) 5- to 10-membered non-aromatic heterocycle and (iii) 7- to 10-membered bridged heterocycle.

Examples of the "5- to 14-membered (preferably 5- to 10-membered) aromatic heterocycle" described above include aromatic heterocycle such as thiophene, benzo[b]thiophene, benzo[b]furan, benzimidazole, benzoxazole, benzothiazole, benzoisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazane, phenoxazine, and the like; or the ring produced by condensing the aromatic heterocycle (preferably monocyclic heterocycle) with 1 or more (preferably 1 or 2) aromatic ring(s) (e.g., benzene ring, and the like); and the like.

Examples of the "5- to 10-membered non-aromatic heterocycle" described above include pyrrolidine, imidazoline, pyrazolidine, pyrazoline, piperidine, piperazine, morpholine, thiomorpholine, dioxazole, oxadiazoline, thiadiazoline, triazoline, thiadiazole, dithiazole, and the like.

Examples of the "7- to 10-membered bridged heterocycle" described above include quinuclidine, 7-azabicyclo[2.2.1]heptane, and the like.

Preferable examples of the "heterocyclic group" include 5- to 14-membered (preferably 5- to 10-membered) (monocyclic or bicyclic) heterocyclic group containing 1 to 4 heteroatom(s) selected from 1 or 2 kind(s) of atoms which are nitrogen atom, sulfur atom and oxygen atom in addition to carbon atom(s). Concrete examples are aromatic heterocyclic group such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, and the like; non-aromatic heterocyclic group such as 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidinyl, 3-piperidinyl, 4-piperidinyl, 1-piperazinyl, 2-piperazinyl, morpholino, thiomorpholino, and the like.

Among them, 5- or 6-membered heterocyclic group containing 1 to 3 heteroatom(s) selected from nitrogen atom, sulfur atom and oxygen atom in addition to carbon atom(s) and the like are more preferable. Concrete examples are 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidinyl, 3-piperidinyl, 4-piperidinyl, 1-piperazinyl, 2-piperazinyl, morpholino, thiomorpholino, and the like.

The "substituent" of the "optionally substituted heterocyclic group" has the same meaning as the "substituent" of the "optionally substituted hydrocarbyl" described above.

The "heterocyclic group" may have 1 to 5, preferably 1 to 3, substituent(s) as mentioned above at possible positions and, when the number of substituents is two or more, those substituents may be the same as or different from one another.

In this specification the "acyl" includes, for example, formyl, $C_{1-6}$ alkyl-carbonyl (e.g., acetyl, propionyl, etc.), $C_{3-6}$ cycloalkyl-carbonyl (e.g., cyclopropylcarbonyl, cyclobutylcarbonyl, cyclopentylcarbonyl, cyclohexylcarbonyl, etc.), $C_{1-6}$ alkoxy-carbonyl (e.g., methoxycarbonyl, ethoxycarbonyl, etc.), $C_{6-14}$ aryl-carbonyl (e.g., benzoyl, etc.), $C_{7-16}$ aralkyl-carbonyl (e.g., phenylacetyl, 3-phenylpropionyl, etc.), $C_{6-14}$ aryloxy-carbonyl (e.g., phenoxycarbonyl, etc.), $C_{7-16}$ aralkyloxy-carbonyl (e.g., benzyloxycarbonyl, etc.), 5- or 6-membered heterocyclic-carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-14}$ aryl-carbamoyl (e.g., phenylcarbamoyl, 1-naphthylcarbamoyl, etc.), $C_{1-6}$ alkoxy-carbamoyl (e.g., methoxycarbamoyl, ethoxycarbamoyl, etc.), 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), $C_{1-6}$ alkylsulfinyl (e.g., methylsulfinyl, ethylsulfinyl, propylsulfinyl, butylsulfinyl etc.), $C_{6-14}$ arylsulfinyl (e.g., phenylsulfinyl, etc.), $C_{1-6}$ alkylsulfonyl (e.g., methylsulfonyl, ethylsulfonyl, propylsulfoyl, butylsulfonyl, etc.), $C_{6-14}$ arylsulfinyl (e.g., phenylsulfinyl, etc.) and the like.

$R^1$ in the formula (I) is (1) an optionally substituted hydrocarbyl, (2) an amino substituted with one or two substituents selected from an optionally substituted hydrocarbyl and an optionally substituted heterocyclic group, (3) an optionally substituted cyclic amino, (4) an optionally substituted heterocyclic group, (5) an acyl, or (6) an optionally substituted hydrocarbyloxy.

Examples of the "cyclic amino" in the "optionally substituted cyclic amino" for $R^1$ include a 3- to 7-membered cyclic amino such as aziridino, pyrrolidino, imidazolidino, oxazolidino, thiazolidino, piperidino, 1,2-dihydropyridyl, 1,2,3,6-tetrahydropyridyl, piperazino, morpholino, thiomorpholino, and the like.

The "substituent" of the "optionally substituted cyclic amino" has the same meaning as the "substituent" of the "optionally substituted hydrocarbyl" described above.

The "cyclic amino" may have 1 to 3 substituent(s) as mentioned above at possible positions and, when the number of substituents is two or more, those substituents may be the same as or different from one another.

Examples of the "hydrocarbyloxy" of the "optionally substituted hydrocarbyloxy" for $R^1$ include $C_{1-8}$ alkoxy (e.g., methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, heptyloxy, octyloxy, etc.), a $C_{2-8}$ alkenyloxy (e.g., vinyloxy, allyloxy, 1-propenyloxy, 2-methyl-1-propenyloxy, 1-butenyloxy, 2-butenyloxy, 3-butenyloxy, 3-methyl-2-butenyloxy, 1-pentenyloxy, 2-pentenyloxy, 3-pentenyloxy, 4-pentenyloxy, 4-methyl-3-pentenyloxy, 1-hexenyloxy, 2-hexenyloxy, 3-hexenyloxy, 4-hexenyloxy, 5-hexenyloxy, 1-heptenyloxy, 1-octenyloxy, etc.), a $C_{2-8}$ alkynyloxy (e.g., ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1-hexynyloxy, 2-hexynyloxy, 3-hexynyloxy, 4-hexynyloxy, 5-hexynyloxy, 1-heptynyloxy, 1-octynyloxy, etc.), a $C_{2-8}$ alkadienyloxy (e.g., 2,4-hexadienyloxy, etc.), a $C_{2-8}$ alkadiynyloxy (e.g., 2,4-hexadiynyloxy, etc.), a $C_{3-7}$ cycloalkyloxy (e.g., cyclopropyloxy, cyclobutyloxy, cyclopentyloxy, cyclohexyloxy, cycloheptyloxy, etc.), a $C_{3-7}$ cycloalkenyloxy (e.g., 1-cyclopentenyloxy, 2-cyclopentenyloxy, 3-cyclopentenyloxy, 1-cyclohexenyloxy, 2-cyclohexenyloxy, 3-cyclohexenyloxy, 1-cycloheptenyloxy, 2-cycloheptenyloxy, 3-cycloheptenyloxy, etc.), a $C_{3-7}$ cycloalkadienyloxy (e.g., 2,4-cycloheptadienyloxy, etc.), a partly saturated and fused bicyclic hydrocarbyloxy, preferably, $C_{9-10}$ partly saturated and fused bicyclic hydrocarbyloxy, etc. (including those where the benzene ring is combined to 5- or 6-membered non-aromatic cyclic hydrocarbon group as a ring system) (e.g., 1-indenyloxy, 2-indenyloxy, 1-indanyloxy, 2-indanyloxy, 1,2,3,4-tetrahydro-1-naphthyloxy, 1,2,3,4-tetrahydro-2-naphthyloxy, 1,2-dihydro-1-naphthyloxy, 1,2-dihydro-2-naphthyloxy, 1,4-dihydro-1-naphthyloxy, 1,4-dihydro-2-naphthyloxy, 3,4-dihydro-1-naphthyloxy, 3,4-dihydro-2-naphthyloxy, etc.), a $C_{3-7}$ cycloalkyl-$C_{1-4}$ alkoxy, a $C_{3-7}$ cycloalkenyl-$C_{1-4}$ alkoxy, a $C_{3-7}$ cycloalkyl-$C_{2-4}$ alkenyloxy, a $C_{3-7}$ cycloalkenyl-$C_{2-4}$ alkenyloxy, a $C_{9-10}$ partly saturated and fused bicyclic hydrocarbon-$C_{1-4}$ alkoxy, a $C_{9-10}$ partly saturated and fused bicyclic hydrocarbon-$C_{2-4}$ alkenyloxy (e.g., cyclopropylmethyloxy, cyclopropylethyloxy, cyclobutylmethyloxy, cyclobutylethyloxy, cyclopentylmethyloxy, 2-cyclopentenylmethyloxy, 3-cyclopentenylmethyloxy, cyclopentylethyloxy, cyclohexylmethyloxy, 2-cyclohexenylmethyloxy, 3-cyclohexenylmethyloxy, cyclohexylethyloxy, cycloheptylmethyloxy, cycloheptylethyloxy, 2-(3,4-dihydro-2-naphtyl)ethyloxy, 2-(1,2,3,4-tetrahydro-2-naphtyl)ethyloxy, 2-(3,4-dihydro-2-naphtyl)ethenyloxy, etc.), a $C_{6-10}$ aryloxy (including that where a 5- to 6-membered non-aromatic hydrocarbon ring is fused with phenyl) (e.g., phenyloxy, α-naphthyloxy, β-naphthyloxy, 4-indenyloxy, 5-indenyloxy, 4-indanyloxy, 5-indanyloxy, 5,6,7,8-tetrahydro-1-naphthyloxy, 5,6,7,8-tetrahydro-2-naphthyloxy, 5,6-dihydro-1-naphthyloxy, 5,6-dihydro-2-naphthyloxy, 5,6-dihydro-3-naphthyloxy, 5,6-dihydro-4-naphthyoxyl, etc.), a $C_{7-14}$ aralkyloxy (e.g., benzyloxy, phenethyloxy, 1-phenylethyloxy, 1-phenylpropyloxy, 2-phenylpropyloxy, 3-phenylpropyloxy, α-naphthylmethyloxy, α-naphthylethyloxy, β-naphthylmethyloxy, β-naphthylethyloxy, styryloxy, cinnamyloxy, etc.), and the like.

The "substituent" of the "optionally substituted hydrocarbyloxy" has the same meaning as the "substituent" of the "optionally substituted hydrocarbyl" described above.

The "hydrocarbyloxy" may have 1 to 5, preferably 1 to 3, substituent(s) as mentioned above at possible positions and, when the number of substituents is two or more, those substituents may be the same as or different from one another.

$R^1$ is preferably (1) an optionally substituted hydrocarbyl, or (2) an amino substituted with two substituents selected from an optionally substituted hydrocarbyl. More preferred is an optionally substituted $C_{3-10}$ alkyl, an optionally substituted $C_{3-10}$ alkenyl or an amino substituted with two optionally substituted $C_{1-4}$ alkyls. $R^1$ is more preferably (i) a $C_{3-10}$ alkyl optionally substituted with hydroxy or $C_{1-6}$ alkyl-carbonyloxy, (ii) $C_{3-10}$ alkenyl, or (iii) a di-$C_{1-4}$ alkylamino.

$R^2$ is an aromatic group substituted with one or two substituents at the positions adjacent to the position bonded to Z, and said aromatic group may have additional substituent(s).

Examples of the "aromatic group" of the "aromatic group substituted with one or two substituents at the positions adjacent to the position bonded to Z, and said aromatic group may have additional substituent(s)" for $R^2$ include a $C_{6-14}$ aryl (e.g., phenyl, 1-naphthyl, 2-naphthyl, 2-biphenyl, 3-biphenyl, 4-biphenyl, etc.), a 5- or 6-membered aromatic heterocyclic group (e.g., furyl, thienyl, 1- or 3-pyrrolyl, 2-oxazolyl, 3-isoxazolyl, thiazolyl, 3-isothiazolyl, 1- or 2-imidazolyl, 1-pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, 2-, 3- or 4-pyridyl, 2- or 4-pyrimidinyl, 3-pyridazinyl, pyrazinyl, triazinyl, etc.), a 8- to 12-membered bicyclic or tricyclic fused aromatic heterocyclic group (e.g., benzofuranyl, isobenzofuranyl, benzothienyl, indolyl, isoindolyl, 1H-indazolyl, benzindazolyl, benzoxazolyl, 1,2-benzisoxazolyl, benzothiazolyl, benzopyranyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.), and the like. Among others preferred is $C_{6-10}$ aryl, 5- or 6-membered aromatic heterocyclic group, and the like. More preferred is phenyl, pyridyl, etc. Especially, phenyl is preferable.

The "substituent" of the "aromatic group substituted with one or two substituents at the positions adjacent to the position bonded to Z, and said aromatic group may have additional substituent(s)" has the same meaning as the "substituent" of the "optionally substituted hydrocarbyl" described above, with the proviso that oxo, imino and $C_{1-6}$ alkylimino are excluded.

The "aromatic group" may have 1 to 5, preferably 1 to 3, substituent(s) as mentioned above at the positions adjacent to the position bonded to Z and possible positions and, when the number of substituents is two or more, those substituents may be the same as or different from one another.

$R^2$ is preferably (i) 2,4,6-trisubstituted phenyl, (ii) 2,4-disubstituted phenyl, (iii) 2,4,6-trisubstituted 3-pyridyl, (iv) 2,6- or 4,6-disubstituted 3-pyridyl, or (v) 3,5-disubstituted 2-pyridyl. Among others, preferred substituents include, for example, halogen atom, an optionally substituted $C_{1-4}$ alkyl (e.g., optionally halogenated $C_{1-4}$ alkyl, etc.), an optionally substituted $C_{1-4}$ alkoxy (e.g., optionally halogenated $C_{1-4}$ alkoxy, etc.), an optionally substituted amino (e.g., mono- or di-$C_{1-4}$ alkylamino, etc.), acyl (e.g., optionally halogenated $C_{1-4}$ alkyl-carbonyl, etc.), cyano, and the like. More preferable substituents are halogen atom and optionally halogenated $C_{1-4}$ alkyl.

X is (1) —$NR^3$— wherein $R^3$ is a hydrogen, an optionally substituted hydrocarbyl or an acyl, or (2) sulfur.

X is preferably —$NR^3$— wherein $R^3$ is a hydrogen, an optionally substituted hydrocarbyl or an acyl. Among them, the preferable X is —NH— or —N(optionally substituted $C_{1-6}$ alkyl)-. The most preferable X is —N($CH_3$)—.

$Y^1$, $Y^2$ and $Y^3$ are each an optionally substituted methine or a nitrogen, provided that one or less of $Y^1$, $Y^2$ and $Y^3$ is nitrogen.

The substituents of the "optionally substituted methine" for $Y^1$, $Y^2$ and $Y^3$ include, for example, (1) an optionally substituted hydrocarbyl, (2) an optionally substituted amino, (3) an optionally substituted heterocyclic group, (4) an acyl, (5) an optionally substituted hydrocarbyloxy, (6) halogen, (7) nitro, (8) cyano, and the like.

Examples of the substituents of the "optionally substituted amino" of above-mentioned (2) include an optionally substituted hydrocarbyl or an acyl.

Examples of the "optionally substituted hydrocarbyloxy" of above-mentioned (5) include the same group as the optionally substituted hydrocarbyloxy for $R^1$.

The preferred substituents of the "optionally substituted methine" for $Y^1$, $Y^2$ and $Y^3$ are halogen, $C_{1-4}$ alkoxy, $C_{1-4}$ alkyl, cyano, etc.

Each of $Y^1$, $Y^2$ and $Y^3$ is preferably CH.

Z is an optionally substituted methylene, provided that carbonyl is excluded.

The substituents of the "optionally substituted methylene" for Z has the same meaning as the "substituent" of the "optionally substituted hydrocarbyl" described above.

Z is preferably a methylene, a hydroxymethyl, etc.

Preferred examples of the Compound (I) include a compound wherein $R^1$ is an optionally substituted $C_{3-10}$ alkyl, an optionally substituted $C_{3-10}$ alkenyl or an amino substituted with two optionally substituted $C_{1-4}$ alkyls;

$R^2$ is (i) 2,4,6-trisubstituted phenyl, (ii) 2,4-disubstituted phenyl, (iii) 2,4,6-trisubstituted 3-pyridyl, (iv) 2,6- or 4,6-disubstituted 3-pyridyl, or (v) 3,5-disubstituted 2-pyridyl;

X is —NH— or —N (optionally substituted $C_{1-6}$ alkyl)-;

Each of $Y^1$, $Y^2$ and $Y^3$ is CH; and

Z is a methylene or a hydroxymethylene.

More preferred examples of the Compound (I) include a compound wherein $R^1$ is (i) $C_{3-10}$ alkyl which may be substituted with one or two substituents selected from the group consisting of hydroxy, and $C_{1-6}$ alkyl-carbonyloxy, (ii) $C_{2-6}$ alkenyl or (iii) a di-$C_{1-4}$ alkylamino;

$R^2$ is a (i) 2,4,6-trisubstituted phenyl, (ii) 2,4-disubstituted phenyl, (iii) 2,4,6-trisubstituted 3-pyridyl, (iv) 2,6- or 4,6-disubstituted 3-pyridyl, or (v) 3,5-disubstituted 2-pyridyl group, wherein the substituents are selected from the group consisting of halogen atom, an optionally substituted $C_{1-4}$ alkyl (e.g., optionally halogenated $C_{1-4}$ alkyl, etc.), an optionally substituted $C_{1-4}$ alkoxy (e.g., optionally halogenated $C_{1-4}$ alkoxy, etc.), an optionally substituted amino. (e.g., mono- or di-$C_{1-4}$ alkylamino, etc.), acyl (e.g., optionally halogenated $C_{1-4}$ alkyl-carbonyl, etc.) and cyano;

X is —NH— or —N(optionally halogenated $C_{1-6}$ alkyl)-;

each of $Y^1$, $Y^2$ and $Y^3$ is CH; and

Z is methylene or hydroxymethylene.

Much more preferred examples of the Compound (I) include a compound wherein $R^1$ is (1) $C_{3-10}$ alkyl optionally substituted with hydroxy or $C_{1-6}$ alkyl-carbonyloxy, (2) $C_{3-10}$ alkenyl or (3) di-$C_{1-4}$ alkylamino;

$R^2$ is 2,4,6-trisubstituted phenyl, wherein the substituent is selected from the group consisting of (1) halogen atom and (2) optionally halogenated $C_{1-4}$ alkyl;

X is —N($C_{1-6}$ alkyl)-;

$Y^1$ is CH;

$Y^2$ is CH;

$Y^3$ is CH; and

Z is a methylene or a hydroxymethylene.

Especially, preferable examples of the Compound (I) are
(1) N,N-diethyl-2-(mesitylmethyl)-1-methyl-1H-benzimidazol-7-amine;
(2) 2-[2,6-dichloro-4-(trifluoromethyl)benzyl]-N,N-diethyl-1-methyl-1H-benzimidazol-7-amine;
(3) 3-[2-(mesitylmethyl)-1-methyl-1H-benzimidazol-7-yl] pentan-3-ol;
(4) 7-[1-ethylprop-1-en-1-yl]-2-(mesitylmethyl)-1-methyl-1H-benzimidazole;
(5) 7-(1-ethylpropyl)-2-(mesitylmethyl)-1-methyl-1H-benzimidazole;
(6) 3-{2-[2,6-dichloro-4-(trifluoromethyl)benzyl]-1-methyl-1H-benzimidazol-7-yl}pentan-3-ol;
(7) 2-[2,6-dichloro-4-(trifluoromethyl)benzyl]-7-[1-ethylprop-1-en-1-yl]-1-methyl-1H-benzimidazole;
(8) 2-{2-[2,6-dichloro-4-(trifluoromethyl)benzyl]-1-methyl-1H-benzimidazol-7-yl}-1-methylbutyl acetate;
(9) 3-{2-[2,6-dichloro-4-(trifluoromethyl)benzyl]-1-methyl-1H-benzimidazol-7-yl}pentan-2-ol;
(10) [7-(1-ethylpropyl)-1-methyl-1H-benzimidazol-2-yl] (mesityl)methanol; or a salt thereof.

A salt of a compound of the formula (I) includes, for example, a metal salt, an ammonium salt or a salt with an organic base, a salt with an inorganic acid, an organic acid, or a basic or acidic amino acid. Preferable examples of a metal salt include alkali metal salts such as a sodium salt or a potassium salt; alkaline earth metal salts such as a calcium salt, a magnesium salt or a barium salt; and an aluminum salt. Preferable examples of a salt with an organic base include salts with trimethylamine, triethylamine, pyridine, picoline, ethanolamine, diethanolamine, triethanolamine, dicyclohexylamine, and N,N-dibenzylethylenediamine. Preferable examples of a salt with an inorganic acid include salts with hydrochloric acid, hydrobromic acid, nitric acid, sulfuric acid and phospholic acid. Preferable examples of a salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Preferable examples of a salt with basic amino acid include salts with arginine, lysine and ornithine. Preferable examples of a salt with an acidic amino acid include salts with aspartic acid and glutamic acid.

Among them, pharmaceutically acceptable salts are preferable. Examples thereof include inorganic salts such as alkali metal salts (e.g., sodium salt, potassium salt etc.) or alkaline earth metal salts (e.g., calcium salt, magnesium salt, barium salt etc.) and an ammonium salt when the compound has an acidic functional group, and inorganic salts such as hydrochloride, sulfate, phosphate or hydrobromide and organic salts such as acetate, maleate, fumarate, succinate, methanesulfonate, p-toluenesulfonate, citrate or tartrate when the compound has a basic functional group.

Compound (I) may be a hydrate or a non-hydrate. The hydrate is exemplified by semihydrate, monohydrate, sesquihydrate and dihydrate. Compound (I) may be a solvate or a non-solvate.

Compound (I) labeled by an isotope (e.g., $^2H$, $^3H$, $^{14}C$, $^{35}S$, $^{125}I$) is encompassed within Compound (I).

When Compound (I) is present as a configuration isomer, diastereomer, conformer and the like, then it can be isolated if desired by an ordinary separation or purification procedure.

When Compound (I) is present as a racemate, it can be resolved into S form and R form by an ordinary optical resolution method.

When Compound (I) has its stereoisomers, then individual isomers or a mixture thereof may also be encompassed in this invention.

Compound (I) may be in the form of a prodrug thereof.

The prodrug of Compound (I) refers to a compound that is converted into Compound (I) by a reaction with an enzyme, gastric acid, or the like under a physiological condition in the living body, namely, (i) a compound that is converted into Compound (I) by an enzymatic oxidation, reduction, hydrolysis, or the like, and (ii) a compound that is converted into Compound (I) by hydrolysis with gastric acid or the like. Examples of a prodrug of Compound (I) to be used include a compound or its salt wherein hydroxy in Compound (I) is acylated, alkylated, phosphorylated, or converted into borate (e.g., a compound or its salt wherein hydroxy in Compound (I) is converted into acetyloxy, palmitoyloxy, propanoyloxy, pivaloyloxy, succinyloxy, fumaryloxy, alanyloxy, dimethylaminomethylcarbonyloxy, etc.), a compound or its salt wherein carboxy in Compound (I) is esterified or amidated (e.g., a compound or its salt wherein carboxy in Compound (I) is subjected to ethyl esterification, phenyl esterification, dimethylaminomethyl esterification, pivaloyloxymethyl esterification, ethoxycarbonyloxyethyl esterification, phthalidyl esterification, (5-methyl-2-oxo-1,3-dioxolan-4-yl)methyl esterification, cyclohexyloxycarbonyl esterification, or conversion into the methyl amide, etc.), or the like. These prodrugs can be produced according to a per se known method or its modified method.

Further, a prodrug of Compound (I) may be a compound or its salt that is converted into Compound (I) under physiological conditions as described in "Development of Drugs", Volume 7, Molecular Design, Hirokawa Shoten, 1990; pages 163-198.

General Synthetic Method

Production of a Compound (I) is disclosed below. The following examples are given to illustrate the invention and are not intended to be inclusive in any manner. Alternative methods may be employed by one skilled in the art, and substituents of Compound (I) may be converted to other substituents by known arts.

A process for preparing Compound (I) is shown in the following methods. In the schemes, the compound may contain salt forms, and examples of the salts are the same as salts of Compound (I) and the like. The sequence of each step for preparing Compound (I) may be changed. Each of the materials in the schemes can be used as it is when it can be commercially available, and it can be produced in accordance with the known methods per se or analogous methods thereof.

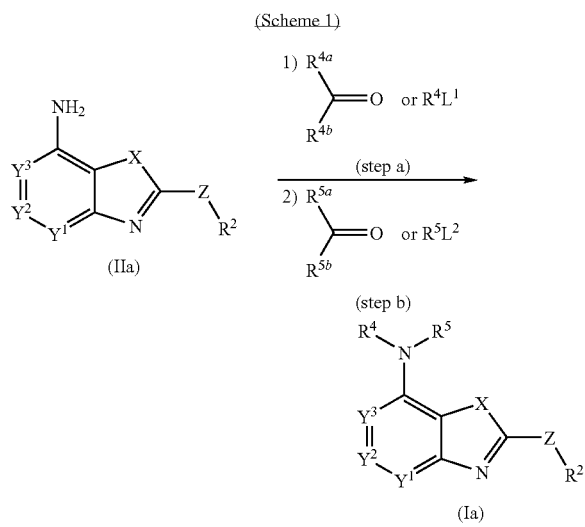

wherein $R^4$ and $R^5$ are independently an optionally substituted hydrocarbyl, $R^{4a}$, $R^{4b}$, $R^{5a}$ and $R^{5b}$ are independently hydrogen or an optionally substituted hydrocarbyl, $L^1$ and $L^2$ are independently a leaving group including a halogen atom such as chlorine, bromine and iodine, sulfonyloxy such as p-toluenesulfonyloxy, methanesulfonyloxy and trifluoromethanesulfonyloxy, etc. and acyloxy such as acetyloxy and benzoyloxy, etc., and each of other symbols has the meaning defined above. Preparation of compound (IIa) is described in Scheme 4.

Compound (Ia), which is encompassed within Compound (I), can be prepared from compound (IIa) by reductive alkylation with $R^{4a}R^{4b}C=O$ or $R^{5a}R^{5b}C=O$ or alkylation with $R^4L^1$ or $R^5L^2$. The reductive alkylation may be performed by in situ production of an imine which is then reduced by an appropriate reducing agent or hydrogenation in the presence of a hydrogenation catalyst. In the first alkylation, $R^{4a}R^{4b}C=O$ or $R^4L^1$ may be used, and $R^{5a}R^{5b}C=O$ or $R^5L^2$ may be used in the second alkylation. When $R^4$ is equal to $R^5$ in compound (Ia), $R^{4a}R^{4b}C=O$ or $R^4L^1$ may be used for the second alkylation which may be performed either one pot in step a or stepwise in step b.

When $R^{4a}R^{4b}C=O$ or $R^{5a}R^{5b}C=O$ is employed, 1 to excess, preferably 1 to 20 moles of a compound represented by $R^{4a}R^{4b}C=O$ or a salt thereof or $R^{5a}R^{5b}C=O$ or a salt thereof are employed per 1 mole of compound (IIa).

A reducing agent is preferably sodium borohydride, lithium borohydride, sodium cyanoborohydride and sodium triacetoxyborohydride, and 1 to 20 moles, preferably 1 to 10 moles of a reducing agent is employed per 1 mole of compound (IIa).

A hydrogenation catalyst is preferably a palladium catalyst such as palladium black, palladium oxide, palladium barium sulfate, palladium on carbon, palladium hydroxide, a platinum catalyst such as platinum black, platinum oxide and platinum on carbon, or nickel catalyst such as reduced nickel, oxidized nickel or Raney nickel.

Examples of the solvents having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as 1,2-dichloroethane, chloroform and dichloromethane, nitriles such as acetonitrile, amides such as N,N-dimethylformamide, N,N-dimethylacetamide and 1-methyl-2-pyrrolidinone, ketones such as acetone and 2-butanone, sulfoxides such as dimethylsulfoxide and acids such as acetic acid. These solvents may be used by mixing at an appropriate ratio, or may not be used.

When producing an imine, use of molecular sieves or addition of an acid such as acetic acid and trifluoroacetic acid, etc., or a Lewis acid such as trihalogenated boron (e.g., boron trichloride and boron trifluoride), tetrahalogenated titanium (e.g., titanium tetrachloride, titanium tetrabromide and titanium(IV) isopropoxide) and halogenated aluminium (e.g., aluminium chloride and aluminium bromide) serves to promote the reaction.

While the reaction temperature in this imine production may vary depending on compound (IIa) or a salt thereof as well as other conditions, it is −50 to 150° C., preferably 0 to 100° C. The reaction time is 30 min to 48 hr, preferably 1 hr to 24 hr.

When $R^4L^1$ or $R^5L^2$ is employed, 1 to 10 moles, preferably 1 to 5 moles of a compound represented by $R^4L^1$ or $R^5L^2$ or a salt thereof and 1 to 10 moles, preferably 1 to 3 moles of a base are employed per 1 mole of compound (IIa).

A base may, for example, be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc. and a cyclic amine such as pyridine, etc.

Examples of solvents having no adverse effect on the reaction include alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as 1,2-dichloroethane, chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (IIa) as well as other reaction conditions, it is −20 to 200° C., preferably 0 to 150° C. The reaction time is 5 min to 48 hr, preferably 5 min to 24 hr.

The thus obtained compound (Ia), which is encompassed within Compound (I), can be isolated and purified by known isolating and purifying methods, for example, concentration, concentration under reduced pressure, extraction with solvents, crystallization, recrystallization, transfer dissolution and chromatography.

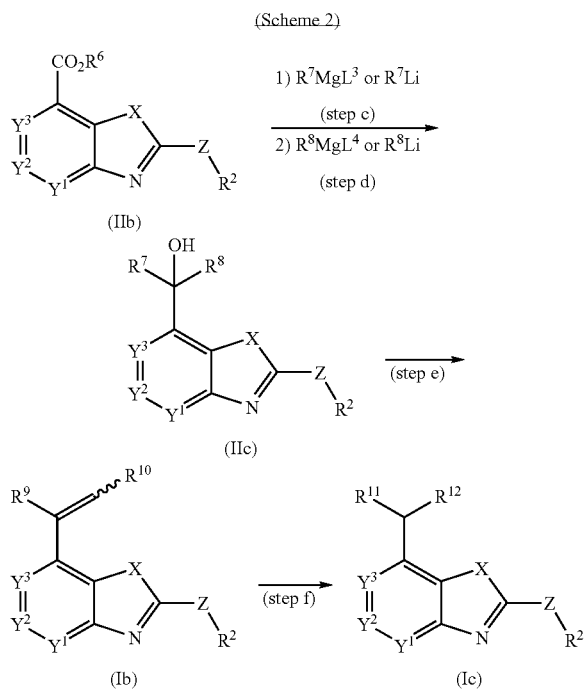

(Scheme 2)

wherein $R^6$, $R^8$, $R^9$, $R^{10}$, $R^{11}$ and $R^{12}$ are independently hydrogen or a optionally substituted hydrocarbyl, $R^7$ is an optionally substituted hydrocarbyl, $R^{11}$ may be equal to $R^7$, $R^{12}$ may be equal to $R^8$, $L^3$ and $L^4$ are independently a halogen atom such as chlorine, bromine and iodine, and each of other symbols has a meaning defined above. Preparation of compound (IIb) is described in Scheme 4.

Compound (IIc) can be prepared from compound (IIb) by Grignard reaction with Grignard reagents or alkylation with alkyl lithium. When $R^8$ is an optionally substituted hydrocarbyl, $R^7MgL^3$ or $R^7Li$ may be used in the first alkylation, and $R^8MgL^4$ or $R^8Li$ may be used in the second alkylation. When $R^7$ is equal to $R^8$ in compound (IIc), $R^7MgL^3$ or $R^7Li$ may be used for the second alkylation which may be performed either one pot in step c or stepwise in step d. When $R^8$ is hydrogen, compound (IIc) can be prepared from compound (IIb) without step d.

When $R^7MgL^3$ and $R^8MgL^4$ are employed, 1 to 20 moles, preferably 1 to 10 moles of a compound represented by $R^7MgL^3$ and $R^8MgL^4$ are employed per 1 mole of compound (IIb).

Examples of the solvents having no adverse effect on the reaction include ethers such as diethyl ether, dioxane and tetrahydrofuran, aromatic hydrocarbons such as benzene, toluene and xylene, halogenated hydrocarbons such as 1,2-dichloroethane, chloroform and dichloromethane, ketones such as acetone and 2-butanone and sulfoxides such as dimethylsulfoxide. These solvents may be used by mixing at an appropriate ratio, or may not be used.

While the reaction temperature may vary depending on compound (IIb) or a salt thereof as well as other reaction conditions, it is −20 to 150° C., preferably 0 to 100° C. The reaction time is 5 min to 48 hr, preferably 5 min to 24 hr.

When $R^7Li$ and $R^8Li$ are employed, 1 to 20 moles, preferably 1 to 10 moles of a compound represented by $R^7Li$ and $R^8Li$ are employed per 1 mole of compound (IIb) or a salt thereof.

Examples of the solvents having no adverse effect on the reaction include ethers such as diethyl ether, dioxane and tetrahydrofuran, aromatic hydrocarbons such as benzene, toluene and xylene, halogenated hydrocarbons such as 1,2-dichloroethane, chloroform and dichloromethane, ketones such as acetone and 2-butanone and sulfoxides such as dimethylsulfoxide. These solvents may be used by mixing at an appropriate ratio, or may not be used.

While the reaction temperature may vary depending on compound (IIb) or a salt thereof as well as other reaction conditions, it is −100 to 150° C., preferably −80 to 100° C. The reaction time is 5 min to 48 hr, preferably 5 min to 24 hr.

The thus obtained compound (IIc) can be isolated and purified by known isolating and purifying methods, for example, concentration, concentration under reduced pressure, extraction with solvents, crystallization, recrystallization, transfer dissolution and chromatography.

Compound (Ib), which is encompassed within Compound (I), can be prepared by dehydration of compound (IIc) with an acid.

An acid may, for example, be an inorganic acid such as hydrochloric acid, sulfuric acid, nitric acid and thionyl chloride, etc., and an ordinary organic acid such as formic acid, acetic acid, trifluoroacetic acid and methanesulfonic acid, p-toluenesulfonic acid, etc. as well as a Lewis acid.

In dehydration step, 1 mole to excess of an acid is employed per 1 mole of compound (IIc) or an acid may be employed as a solvent.

Examples of the solvents having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as 1,2-dichloroethane, chloroform and dichloromethane, nitrites such as acetonitrile, amides such as N,N-dimethylformamide, N,N-dimethylacetamide and 1-methyl-2-pyrrolidinone, ketones such as acetone and 2-butanone and sulfoxides such as dimethylsulfoxide. These solvents may be used by mixing at an appropriate ratio, or may not be used.

While the reaction temperature may vary depending on compound (IIc) or a salt thereof as well as other reaction conditions, it is −20 to 200° C., preferably −20 to 150° C. The reaction time is 5 min to 48 hr, preferably 5 min to 24 hr.

The thus obtained olefine can be isolated and purified by known isolating and purifying methods, for example, concentration, concentration under reduced pressure, extraction with solvents, crystallization, recrystallization, transfer dissolution and chromatography.

Compound (Ic), which is encompassed within Compound (I), can be prepared by reduction of compound (Ib) with an appropriate reducing agent or catalytic hydrogenation.

In reduction step, a reducing agent is preferably sodium borohydride, lithium borohydride, sodium cyanoborohydride, sodium triacetoxyborohydride, lithium aluminum hydride, borane such as borane-dimethylsulfide complex and borane-tetrahydrofuran complex, etc.

Catalytic hydrogenation may be performed in this step. A hydrogenation catalyst is preferably a palladium catalyst such as palladium black, palladium oxide, palladium barium sulfate, palladium on carbon, palladium hydroxide, a platinum catalyst such as platinum black, platinum oxide and platinum on carbon, or nickel catalyst such as reduced nickel, oxidized nickel or Raney nickel.

In reducing step, an acid such as acetic acid and trifluoroacetic acid, etc., or a Lewis acid such as trihalogenated boron (e.g., boron trichloride and boron trifluoride), tetrahalogenated titanium (e.g., titanium tetrachloride, titanium tetrabromide and titanium(IV) isopropoxide) and halogenated aluminium (e.g., aluminium chloride and aluminium bromide) may be added to promote the reaction.

In this step, 1 to 20 moles, preferably 1 to 10 moles of a reducing agent are employed per 1 mole of the olefine or a salt thereof.

Examples of the solvents having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as 1,2-dichloroethane, chloroform and dichloromethane, nitrites such as acetonitrile, amides such as N,N-dimethylformamide, N,N-dimethylacetamide and 1-methyl-2-pyrrolidinone, ketones such as acetone and 2-butanone, sulfoxides such as dimethylsulfoxide and acids such as acetic acid. These solvents may be used by mixing at an appropriate ratio.

While the reaction temperature may vary depending on the olefine or a salt thereof as well as other reaction conditions, it is 0 to 150° C., preferably 0 to 100° C. The reaction time is 5 min to 48 hr, preferably 5 min to 24 hr.

The thus obtained compound (Ic) can be isolated and purified by known isolating and purifying methods, for example, concentration, concentration under reduced pressure, extraction with solvents, crystallization, recrystallization, transfer dissolution and chromatography.

Step e and step f, dehydration and reduction, may be carried out one pot, which is that an acid and a reducing agent or a catalyst may simultaneously be employed.

(Scheme 3)

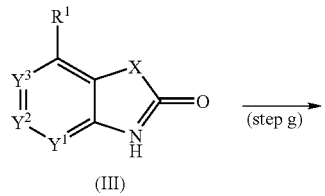

(III)

-continued

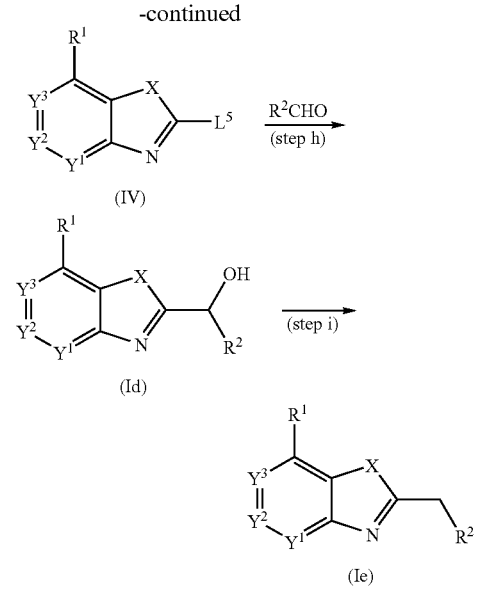

wherein $L^5$ is a leaving group including a halogen atom such as chlorine, bromine and iodine, sulfonyloxy such as p-toluenesulfonyloxy, methanesulfonyloxy and trifluoromethanesulfonyloxy, etc. and acyloxy such as acetyloxy and benzoyloxy, etc., and each of other symbols has the meaning defined above.

Compound (IV) can be prepared by halogenation, sulfonylation or acylation of compound (III) with a halogenation agent, a sulfonylation agent or an acylation agent, respectively.

Examples of a halogenation agent include phosphorus oxychloride, phosphorus oxybromide, phosphorus trichloride, phosphorus tribromide, phosphorus pentachloride, chlorine, bromine, sulfuryl chloride and thionyl chloride. The halogenation agent is employed in an amount of 1 mole to excess per 1 mole of compound (III) or as a solvent.

Examples of the solvents having no adverse effect on the reaction include aromatic hydrocarbons such as benzene, toluene and xylene, ethers such as diethyl ether, dioxane and tetrahydrofuran, esters such as ethyl acetate, nitriles such as acetonitrile, halogenated hydrocarbon such as 1,2-dichloroethane, chloroform and dichloromethane, amides such as N,N-dimethylformamide, N,N-dimethylacetamide and 1-methyl-2-pirrolidinone, ketones such as acetone and 2-butanone and sulfoxides such as dimethylsulfoxide. These solvents may be used by mixing at an appropriate ratio.

While the reaction temperature may vary depending on compound (III) or a salt thereof employed as well as other conditions, it is 0 to 200° C., preferably 20 to 150° C. The reaction time is 10 min to 180 hr, preferably 30 min to 96 hr.

Examples of a sulfonylation agent include p-toluenesulfonylchloride, methanesulfonylchloride, trifluoromethanesulfonylchloride, etc. The sulfonylation agent is employed in an amount of 1 to 10 moles, preferably 1 to 5 moles per 1 mole of compound (III).

Examples of an acylation agent include acetylchloride and benzoylchloride, etc. The acylation agent is employed in an amount of 1 to 10 moles, preferably 1 to 5 moles per 1 mole of compound (III).

Examples of the solvents having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as 1,2-dichloroethane, chloroform and dichloromethane, nitriles such as acetonitrile, amides such as N,N-dimethylformamide and N,N-dimethylacetamide and sulfoxides such as dimethylsulfoxide. These solvents may be used by mixing at an appropriate ratio.

While the reaction temperature may vary depending on compound (III) or a salt thereof as well as other conditions, it is 0 to 200° C., preferably 0 to 150° C. The reaction time is 10 min to 24 hr, preferably 30 min to 12 hr.

The thus obtained compound (IV) can be isolated and purified by known isolating and purifying methods, for example, concentration under reduced pressure, extraction with solvents, crystallization, recrystallization, transfer dissolution and chromatography.

Compound (Id), which is encompassed within Compound (I), can be prepared by reacting compound (IV) with an aldehyde represented by $R^2CHO$ or a salt thereof after treating by an organic metal reagent.

An organic metal reagent may be alkyl lithium, such as n-butyl lithium, sec-butyl lithium and tert-butyl lithium, etc. and is employed in an amount of 1 to 10 moles, preferably 1 to 5 moles per 1 mole of compound (IV) or a salt thereof.

Examples of the solvents having no adverse effect on the reaction include hydrocarbons such as pentane, hexane and heptane, aromatic hydrocarbons such as benzene, toluene and xylene, ethers such as diethyl ether, dioxane and tetrahydrofuran, and halogenated hydrocarbon such as 1,2-dichloroethane, chloroform and dichloromethane. These solvents may be used by mixing at an appropriate ratio.

While the reaction temperature may vary depending on compound (IV) or a salt thereof as well as other conditions, it is −100 to 100° C., preferably −80 to 50° C. The reaction time is 10 min to 24 hr, preferably 30 min to 12 hr.

The thus obtained compound (Id) can be isolated and purified by known isolating and purifying methods, for example, concentration under reduced pressure, extraction with solvents, crystallization, recrystallization, transfer dissolution and chromatography.

Compound (Ie), which is encompassed within Compound (I), can be prepared by reduction of compound (Id) with an appropriate reducing agent or catalytic hydrogenation.

A reducing agent is preferably sodium borohydride, lithium borohydride, sodium cyanoborohydride, sodium triacetoxyborohydride, lithium aluminum hydride, borane, triethylsilane, etc.

Catalytic hydrogenation may be performed in this step. A hydrogenation catalyst is preferably a palladium catalyst such as palladium black, palladium oxide, palladium barium sulfate, palladium on carbon, palladium hydroxide, a platinum catalyst such as platinum black, platinum oxide and platinum on carbon, or nickel catalyst such as reduced nickel, oxidized nickel or Raney nickel.

In reducing step, an ordinary organic acid such as formic acid, acetic acid, trifluoroacetic acid and methanesulfonic acid, p-toluenesulfonic acid, etc., an inorganic acid such as hydrochloric acid, sulfuric acid, nitric acid and thionyl chloride, etc., a Lewis acid such as trihalogenated boron (e.g., boron trichloride and boron trifluoride), tetrahalogenated titanium (e.g., titanium tetrachloride, titanium tetrabromide and titanium(IV) isopropoxide) and halogenated aluminium (e.g., aluminium chloride and aluminium bromide) and acid anhydride such as acetic anhydride and trifluoroacetic anhydride may be added to promote the reaction.

In this step, 1 to 20 moles, preferably 1 to 10 moles of a reducing agent are employed per 1 mole of compound (Id) or a salt thereof.

Examples of the solvents having no adverse effect on the reaction include water, alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as 1,2-dichloroethane, chloroform and dichloromethane, nitriles such as acetonitrile, amides such as N,N-dimethylformamide, N,N-dimethylacetamide and 1-methyl-2-pyrrolidinone, ketones such as acetone and 2-butanone, sulfoxides such as dimethylsulfoxide and acids such as acetic acid. These solvents may be used by mixing at an appropriate ratio.

While the reaction temperature may vary depending on compound (Id) or a salt thereof as well as other reaction conditions, it is 0 to 150° C., preferably 0 to 100° C. The reaction time is 5 min to 48 hr, preferably 5 min to 24 hr.

The thus obtained compound (Ie) can be isolated and purified by known isolating and purifying methods, for example, concentration, concentration under reduced pressure, extraction with solvents, crystallization, recrystallization, transfer dissolution and chromatography.

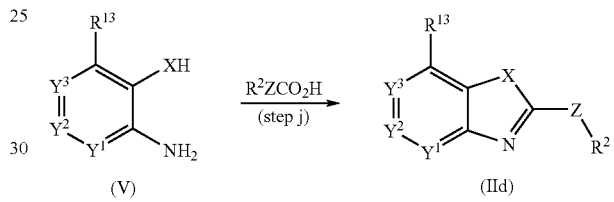

(Scheme 4)

wherein $R^{13}$ is an optionally substituted hydrocarbyl, an optionally substituted amino or ester, and each of other symbols has the meaning defined above.

Compound (IId) can be prepared by cyclization of compound (V).

Examples of the agent for cyclization include N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyldiimidazole, phosphorus oxychloride, phosphorus oxybromide, phosphorus trichloride, phosphorus tribromide, phosphorus pentachloride, polyphosphoric acid, thionyl chloride, sodium hydroxide, potassium hydroxide, etc.

The agent for cyclization is employed in an amount of 1 to 10 moles, preferably 1 to 5 moles per 1 mole of compound (V).

Examples of solvent having no adverse effect on the reaction include alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as 1-methyl-2-pyrrolidinone, N,N-dimethylformamide and N,N-dimethylacetamide, sulfoxides such as dimethylsulfoxide and acids such as acetic acid. These solvents may be used by mixing at an appropriate ratio.

The reaction may be carried out in the presence of an inorganic base or an organic base such as alkali metal salts such as potassium hydroxide, sodium hydroxide, sodium bicarbonate and potassium carbonate, amines such as pyridine, triethylamine, N,N-dimethylaniline and 1,8-diazabicyclo[5.4.0]undec-7-ene, metal hydrides such as potassium hydride and sodium hydride and alkali metal alkoxides such as sodium methoxide, sodium ethoxide and potassium tert-butoxide.

While the reaction temperature may vary depending on the reagent employed as well as other conditions, it is −20 to 200° C., preferably 20 to 150° C. The reaction time is 5 min to 10 hr, preferably 5 min to 2 hr.

The thus obtained compound (IId) can be isolated and purified by known isolating and purifying methods, for example, concentration, concentration under reduced pressure, extraction with solvent, crystallization, recrystallization, transfer dissolution and chromatography.

A starting compound for Compound (I) may be in a form of a salt, including a salt with an inorganic acid (e.g., hydrochloric acid, phosphoric acid, hydrobromic acid and sulfuric acid, etc.) and a salt with an organic acid (e.g., acetic acid, formic acid, propionic acid, fumaric acid, maleic acid, succinic acid, tartaric acid, citric acid, malic acid, oxalic acid, benzoic acid, methanesulfonic acid and benzenesulfonic acid, etc.). When any of these compounds carries an acidic group such as —COOH, etc., a salt with an inorganic base (e.g., an alkaline metal or an alkaline earth metal such as sodium, potassium, calcium and magnesium, ammonia, etc.) or with an organic base (e.g., tri-$C_{1-3}$ alkylamine such as triethylamine, etc.) may be formed.

In each of the reactions described above, when a starting compound carries as a substituent an amino, an amide, a hydrazino, a urea, a carboxy or a hydroxy, then such group may be derivatized with a protective group employed ordinarily in peptide chemistry, which is cleaved after a reaction if desired to yield an intended compound.

A protective group for an amino, an amide and a urea may, for example, be an optionally substituted $C_{1-6}$ alkylcarbonyl (e.g., formyl, methylcarbonyl and ethylcarbonyl, etc.), phenylcarbonyl, a $C_{1-6}$ alkyloxycarbonyl (e.g., methoxycarbonyl, ethoxycarbonyl and tert-butoxycarbonyl, etc.), phenyloxycarbonyl, $C_{7-10}$ aralkylcarbonyl (e.g., benzyloxycarbonyl), $C_{7-10}$ aralkyl (e.g., benzyl, 4-methoxybenzyl, etc.), trityl, phthaloyl, and the like. A substituent on each of the groups listed above may be a halogen atom (e.g., fluorine, chlorine, bromine and iodine), a $C_{1-6}$ alkylcarbonyl (e.g., methylcarbonyl, ethylcarbonyl and butylcarbonyl, etc.) and a nitro, which may occur 1 to about 3 times.

A protective group for a carboxy may, for example, be an optionally substituted $C_{1-6}$ alkyl (e.g., methyl, ethyl, n-propyl, isopropyl, n-butyl, tert-butyl, etc.), phenyl, trityl, silyl, and the like. A substituent on each of the groups listed above may be a halogen atom (e.g., fluorine, chlorine, bromine and iodine), a $C_{1-6}$ alkylcarbonyl (e.g., formyl, methylcarbonyl, ethylcarbonyl, butylcarbonyl, etc.) and a nitro, which may occur 1 to about 3 times.

A protective group for a hydroxy may, for example, be an optionally substituted $C_{1-6}$ alkyl (e.g., methyl, ethyl, n-propyl, isopropyl, n-butyl, tert-butyl, etc.), phenyl, a $C_{7-10}$ aralkyl (e.g., benzyl, 4-methoxybenzyl, etc.), formyl, a $C_{1-6}$ alkyl-carbonyl (e.g., methylcarbonyl, ethylcarbonyl, etc.), phenyloxycarbonyl, $C_{7-10}$ aralkylcarbonyl (e.g., benzyloxycarbonyl, etc.), pyranyl, furanyl, silyl, and the like. A substituent on each of the groups listed above may be a halogen atom (e.g., fluorine, chlorine, bromine and iodine), a $C_{1-6}$ alkyl, phenyl, a $C_{7-10}$ aralkyl, and a nitro, which may occur 1 to about 4 times.

A method for cleaving a protective group is a method known per se or an analogous method, such as a treatment, for example, with an acid, a base, a reduction, UV light, hydrazine, phenylhydrazine, sodium N-methyldithiocarbamate, tetrabutylammonium fluoride, palladium acetate, etc.

Compound (I) has an excellent corticotropin releasing factor antagonistic activity, and when orally administered, Compound (I) shows good pharmacokinetic profiles and exhibits anxiolytic and antidepressive effects to an animal, especially to a mammal (e.g., human, monkey, dog, cat, rabbit, guinea pig, rat, mouse, and the like). Especially, Compound (I) of the present invention shows an excellent solubility profile, an excellent stability in metabolite and an excellent improvement in pharmacokinetics. In addition, Compound (I) is a selective antagonist of CRF1 against a wide range of other receptors and has a low toxicity.

On the basis of that, Compound (I) is useful as a safe pharmaceutical as it is or as formulated with a pharmaceutically acceptable carrier and can be used as a pharmaceutical for preventing and/or treating diseases associated with the functions of a CRF receptor or a CRF, such as depression, major depression, bipolar depression, dysthymia, affective disorder (e.g., seasonal affective disorder), recurrent depression, postpartum depression, suppression symptom, mania, anxiety, generalized anxiety disorder, anxiety syndrome, panic disorder, phobia, social phobia, obsessive-compulsive disorder, posttraumatic stress disorder, stress-induced insomnia, psychic epilepsy, Tourette's syndrome, autism, passion disorder, adjustment disorder, dysthymic disorder, sleep disorder, insomnia, bipolar disorder, circulatory disease, neurosis, schizophrenia, digestive ulcer, irritable bowel syndrome, inflammatory bowel disease, ulcerative colitis, Crohn's disease, stress-induced gastrointestinal disorder, nervous emesis, peptic ulcer, diarrhea, constipation, postoperative ileus, gastrointestine dysfunction and nervous vomiting associated with stress, Alzheimer's disease, Alzheimer's type senile dementia, nervous degenerated disease such as Parkinson's disease and Huntington's disease, multi-infarct dementia, senile dementia, nervous orexia inactivity, eating disorder, anorexia nervosa, hyperphagia and other ingestion disorder, obesity, diabetes, alcohol dependency, pharmacophilia, drug withdrawal, migraine, stress headache, tension headache, ischemic nervous disorder, nervous disorder, cerebral paralysis, progressive supranuclear palsy, amyotrophic lateral sclerosis, multiple sclerosis, muscular convulsion, chronic fatigue syndrome, glaucoma, Meniere syndrome, autonomic imbalance, alopecia, hypertension, cardiovascular disorder, tachycardia, congestive heart attack, hyperphrenia, bronchial asthma, apnea, infant sudden death syndrome, inflammatory disorder, pain, allergic disorder, impotence, menopausal disorder, fertilization disorder, infertility, cancer, immune function abnormality at HIV infection, immune functional abnormality due to stress, cerebrospinal meningitis, acromegaly, incontinence, metabolic syndrome osteoporosis, Cusing syndrome or vascular depression. Especially, Compound (I) can be used as a pharmaceutical for preventing and/or treating affective disorder, depression or anxiety.

When Compound (I) and its prodrug are used as a pharmaceutical for preventing and/or treating diseases described above, the administration route may be oral or parenteral in accordance with the known method per se.

Compound (I) can be formulated with a pharmaceutically acceptable carrier and can be orally or parenterally administered as solid formulations such as tablets, capsules, granules, powders, or the like; or liquid formulations such as syrups, injections, or the like. Also, there can be prepared formulations for transdermal administration such as patchings, cataplasms, ointments (including creams), plasters, tapes, lotions, liquids and solutions, suspensions, emulsions, sprays, and the like.

As for a pharmaceutically acceptable carrier, a variety of organic or inorganic carrier substances, which have been conventionally employed as formulation materials, is used and compounded as a bulking agent, a lubricant, a binding agent, and a disintegrator in solid formulations; a vehicle, a solubilizing agent, a suspending agent, an isotonicity agent, a buffering agent, and an analgesic in liquid formulations. If necessary, formulation excipients such as a preservative, an antioxidant, a stabilizer, a coloring agent, a sweetening agent, and the like can be used.

Preferred examples of the bulking agent include lactose, sucrose, D-mannitol, starch, crystalline cellulose, light anhydrous silicic acid, and the like. Preferred examples of the lubricant include magnesium stearate, potassium stearate, talc, colloidal silica, and the like. Preferred examples of the binding agent include crystalline cellulose, α-starch, sucrose, D-mannitol, dextrin, hydroxypropyl cellulose, hydroxypropylmethyl cellulose, polyvinyl pyrrolidone, and the like. Preferred examples of the disintegrator include starch, carboxymethyl cellulose, calcium carboxymethyl cellulose, croscarmellose sodium, sodium carboxymethyl starch, low-substituted hydroxypropyl cellulose, and the like. Preferred examples of the vehicle include water for injection, alcohol, propylene glycol, macrogol, sesame oil, corn oil, and the like.

If necessary, for the purpose of taste masking, enteric coating, or prolonged action, oral formulations can be prepared by coating by a per se known method. Examples of this coating agent include hydroxypropylmethyl cellulose, ethyl cellulose, hydroxymethyl cellulose, hydroxypropyl cellulose, polyoxyethylene glycol, Tween 80, Pluronic F68 [polyoxyethylene (160) polyoxypropylene (30) glycol], cellulose acetate phthalate, hydroxypropylmethyl cellulose phthalate, hydroxymethyl cellulose acetate phthalate, Eudragit (manufactured by Rohm Company, methacrylic acid-acrylic acid copolymer), and the like.

Preferred examples of the solubilizing agent include polyethylene glycol, propylene glycol, benzyl benzoate, ethanol, trisamiomethane, cholesterol, triethanolamine, sodium carbonate, sodium citrate, and the like. Preferred examples of the suspending agent include surface active agents such as stearyltriethanolamine, sodium lauryl sulfate, laurylaminopropionic acid, lecithin, benzalkonium chloride, benzethonium chloride, glycerin monostearate, and the like; hydrophilic, high molecular substances such as polyvinyl alcohol, polyvinyl pyrrolidone, sodium carboxymethyl cellulose, methyl cellulose, hydroxymethyl cellulose, hydroxyethyl cellulose, hydroxypropyl cellulose, and the like; and so on. Preferred examples of the isotonicity agent include sodium chloride, glycerin, D-mannitol, and the like. Preferred examples of the buffering agent include buffer solutions of a phosphate, an acetate, a carbonate, a citrate, or the like. Preferable examples of the analgesic include benzyl alcohol and the like. Preferred examples of the preservative include paraoxybenzoic acid esters, chlorobutanol, benzyl alcohol, phenethyl alcohol, dehydroacetic acid, sorbic acid, and the like. Preferred examples of the antioxidant include sulfites, ascorbic acid, and the like.

The content of Compound (I) in the composition of the present invention is, for example, about 0.01 to about 100% by weight of the whole preparation.

The dose varies depending on an administration subject, an administration route, disease and the like. For example, when Compound (I) is orally administered to an adult as an antidepressant, Compound (I) as an active ingredient may be administered in an amount of about 0.1 to about 20 mg/kg body weight, preferably about 0.2 to about 10 mg/kg body weight, further preferably about 0.5 to about 10 mg/kg body weight, preferably about 0.5 to about 5 mg/kg body weight. The dose may be administered in one or several divided portions per day.

When the pharmaceutical composition containing Compound (I) of the present invention is used for treatment or/and prevention of the above-mentioned diseases, Compound (I) may be used in combination with another active ingredient. Examples of such a concomitant active ingredient include, for example, benzodiazepines (chlordiazepoxide, diazepam, clorazepate dipotassium, lorazepam, clonazepam, alprazolam etc.), L-type calcium channel blockers (pregabalin etc.), tricyclic or tetracyclic antidepressants (imipramine hydrochloride, amitriptyline hydrochloride, desipramine hydrochloride, clomipramine hydrochloride, carpipramine), selective serotonin reuptake inhibitors (fluvoxamine maleate, fluoxetine hydrochloride, citalopram hydrobromide, sertraline hydrochloride, paroxetine hydrochloride, escitalopram oxalate etc.), serotonin and norepinephrine reuptake inhibitors (venlafaxine hydrochloride, duloxetine hydrochloride etc.), norepinephrine reuptake inhibitors (reboxetine mesilate etc.), mirtazapine, trazodone hydrochloride, nefazodone hydrochloride, bupropion hydrochloride, setiptiline maleate, 5-$HT_{1A}$ agonists (buspirone hydrochloride, tandospirone citrate, osemozotan hydrochloride etc.), 5-$HT_3$ antagonists (cyamemazine etc.), noncardioselective beta-blockers (propranolol hydrochloride, oxprenolol hydrochloride etc.), histamine $H_1$ antagonists (hydroxyzine hydrochloride etc.), antipsychotic agents (chlorpromazine, haloperidol, sulpiride, clozapine, trifluoperazine hydrochloride, fluphenazine hydrochloride, olanzapine, quetiapine fumarate, risperidone, aripiprazole etc.), other anxiolytics (meprobamate), tachykinin antagonist (MK-869 etc.), drugs acting on metabotropic glutamate receptors, CCK antagonists, beta3-adrenocepto agonists (amibegron hydrochloride), GAT-1 inhibitors (tiagabine hydrochloride), N-type calcium channel blockers, carbonic anhydrase type II inhibitors, NMDA glycine site agonists, NMDA antagonist (memantine etc.), peripheral benzodiazepine receptor ligands, vasopressin V1b antagonist, vasopressin V1a antagonist, phosphodiesterase II, IV or X inhibitors, opioid antagonists, uridine, nicotinic receptor agonist, thyroid hormone (T3, T4), TSH, TRH, MAO inhibitors (phenelzine sulfate, tranylcypromine sulfate, moclobemide etc.), 5-$HT_{2A}$ Antagonists, 5-$HT_{2A}$ inverse agonists, a COMT inhibitor (e.g., entacapone etc.), agents for bipolar disorder (lithium carbonate, valproate semisodium, lamotrigine, riluzole, felbamate etc.), cannabinoid CB1 antagonist (rimonabant etc.), sodium channel blockers, anti ADHD drugs (methylphenidate hydrochloride, methamphetamine hydrochloride etc.), agents for alcoholism, agents for autism, agents for chronic fatigue syndrome, agents for fibromyalgia syndrome, agents for agents for epilepsy, agents for insomnia (etizolam, zopiclone, triazolam, zolpidem, ramelteon, indiplon etc.), agents for smoking cessation therapy, agents for narcolepsy, agents for pain, agents for male and female sexual dysfunction, agents for migraine, agents for pathological gambling, agents for restless legs syndrome, agents for substance dependence, agents for irritable bowel syndrome, Alzheimer's disease treating drugs, Parkinson's Disease treating drugs, an amyotrophic lateral sclerosis treating drug (e.g., riluzole etc., neurotrophic factor etc.), a hyperlipidemia treating drug such as a cholesterol lowering drug [statin series (e.g., sodium pravastatin, atorvastatin, simvastatin, rosuvastatin etc.), fibrate (e.g., clofibrate etc.), a squalene synthase inhibitor], agents for treating abnormal behavior or dromomania accompanied with progression of dementia (e.g., sedative, anxiolytic drug etc.), an apoptosis inhibitor, a nerve differentiation/regeneration promoting agent, a hypotensive drug, a diabetes treating drug, anti-obesity drugs, a non-steroidal anti-inflammatory drug (e.g., meloxicam, tenoxicam, indomethacin, ibuprofen, celecoxib, rofecoxib, aspirin, etc.), a disease modifying anti-rheumatoid drug (DMARD), an anti-cytokine drug (e.g., TNF inhibitor, MAP kinase inhibitor etc.), a steroid drug (e.g., dexamethasone, hexestrol, cortisone acetate etc.), sex hormone or a derivative thereof (e.g., progesterone, estradiol, estradiol benzoate etc.), parathyroid hormone (PTH), a calcium receptor antagonist, anticancer drugs, morphine, cannabinoids, etc.

Such another active ingredient and the Compound (I) of the present invention may be mixed according to a known per se method to be formulated into one pharmaceutical composition (e.g., a tablet, powder, a granule, a capsule (including a soft capsule), liquid, a injection, a suppository, a sustained-release preparation etc.), or they may be formulated into separate compositions and then administered to the same subject simultaneously or at a certain interval.

EXAMPLES

The following Reference Examples, Examples and Experiment describe the manner and process of making and using the present invention and are illustrative rather than limiting. It is to be understood that there may be other embodiments which fall within the spirit and scope of the present invention as defined by the claims appended hereto.

In the following examples, the room temperature is ranged between 0 to 30° C., melting points were determined on a Yanaco micro melting point apparatus and were uncorrected. Proton nuclear magnetic resonance ($^1$H-NMR) spectra were recorded on Varian Mercury-300 (300 MHz). Chemical shifts are given in parts per million (ppm) with tetramethylsilane as an internal standard. Abbreviations are used as follows: s=singlet, d=doublet, t=triplet, q=quartet, m=multiplet, dd=doublets of doublet, brs=broad singlet. Coupling constants (J values) are given in hertz (Hz). LC-MS (ESI$^+$) was performed on a Micromass ZMD, using a CAPCELL PAK UG-120 ODS (Shiseido Co., Ltd.) column (2.0 mm i.d.×50 mm) with aqueous MeCN (10-95%) containing 0.05% trifluoroacetic acid, and a HP-1100 (Agilent Technologies) apparatus for monitoring at 220 nm. Reagents and solvents were obtained from commercial sources and used without further purification. Chromatographic purification was carried out on silica gel columns (Kieselgel 60, 0.063-0.22 mm, Merck) or on Purif-Pack (SI 60 µm or NH 60 µm, Fuji Silysia, Ltd.). Preparative TLC purification was conducted using TLC plate (silica gel 60, Merck). Preparative HPLC purification was performed using a Gilson pumping system in conjunction with a photodiode array detector (Hewlett Packard 1100 series) and a Gilson 215 auto sampler. Separations were achieved using an YMC packed column (CombiPrep ODS-A, 5 µm, 50×20 mm) and a linear gradient (90% H$_2$O for 1.0 min, a linear gradient from 10-100% for 3.70 min, then 100% acetonitrile for 2.7 min. 25 mL/min.).

Reference Example 1

N$^2$-Methylbenzene-1,2,3-triamine

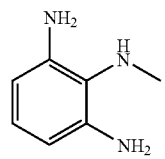

To a suspension of N-methyl-2,6-dinitroaniline (407 mg, 2.06 mmol) in tetrahydrofuran (6.5 mL) was added palladium on carbon (45 mg), and the mixture was purged with hydrogen and stirred under balloon pressure hydrogen for 5 hr at room temperature. The catalyst was removed by filtration, and the filtrate was concentrated in vacuo to give the title compound (280 mg, 2.04 mmol, 99%) as an oil.

$^1$H NMR (DMSO-d$_6$) δ 2.42 (s, 3H), 3.16 (1H, brs), 4.54 (4H, s), 5.88-5.92 (m, 2H), 6.44 (t, J=7.8 Hz, 1H).

Reference Example 2

Methyl 3-amino-2-(methylamino)benzoate

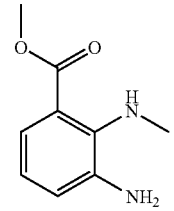

To a suspension of methyl 2-(methylamino)-3-nitrobenzoate (2.10 g, 10.0 mmol) in tetrahydrofuran (40 mL) was added palladium on carbon (210 mg), and the mixture was purged with hydrogen and stirred under balloon pressure hydrogen for 2 hr at room temperature. The catalyst was removed by filtration, and the filtrate was concentrated in vacuo to give the title compound (1.80 g, 10.0 mmol, 100%) as a pale yellow oil.

$^1$H NMR (CDCl$_3$) δ 2.75 (s, 3H), 3.88 (s, 3H), 3.80-3.94 (brs, 2H), 6.06 (brs, 1H), 6.78-6.90 (m, 2H), 7.37 (dd, J=2.6, 7.2 Hz, 1H)

Reference Example 3

2-Bromo-7-(1-ethylpropyl)-1-methyl-1H-benzimidazole

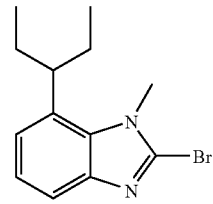

A mixture of 7-(1-ethylpropyl)-1-methyl-1,3-dihydro-2H-benzimidazol-2-one (2.10 g, 10.0 mmol), phosphoric tribromide (5.73 g, 20.0 mmol) and toluene (10 mL) was heated under reflux for 16 hr. The reaction mixture was concentrated in vacuo. The residue was dissolved in saturated sodium hydrogen carbonate solution and ethyl acetate, and extracted. The organics were dried over anhydrous magnesium sulfate, filtered, and concentrated in vacuo. The residue was purified by silica gel column chromatography eluting with a 10-50% ethyl acetate/n-hexane gradient mixture to give the title compound (312 mg, 1.11 mmol, 11%) as colorless oil.

$^1$H NMR (CDCl$_3$) δ 0.83 (t, J=7.2 Hz, 6H), 1.63-1.85 (m, 4H), 3.25-3.31 (m, 1H), 4.03 (s, 3H), 7.11 (dd, J=1.2, 7.8 Hz, 1H), 7.22 (t, J=7.8 Hz, 1H), 7.53 (dd, J=1.2, 7.8 Hz, 1H).

MS Calcd.: 280; MS Found: 281 (M+H).

Reference Example 4

2-(Mesitylmethyl)-1-methyl-1H-benzimidazol-7-amine

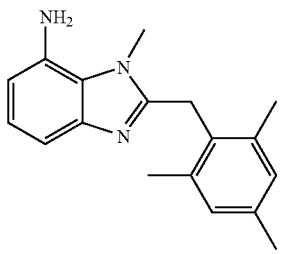

To a solution of mesityleneacetic acid (904 mg, 5.08 mmol) in tetrahydrofuran (20 mL) was added N,N'-carbonyldiimidazole (823 mg, 5.08 mmol) at room temperature. After the mixture was stirred for 1 hr at 50° C., $N^2$-methylbenzene-1,2,3-triamine (700 mg, 5.08 mmol) in tetrahydrofuran (8 mL) was added to the mixture and the mixture was refluxed for further 18 hr. After the mixture was cooled, the solvent was evaporated in vacuo, and the residue was purified by silica gel column chromatography eluting with a 60-80% ethyl acetate/n-hexane gradient mixture to give the title compound (340 mg, 1.22 mmol, 24%) as a colorless solid. The resulting solid was recrystallized from n-hexane/tetrahydrofuran to give the title compound (254 mg, 0.85 mmol).

mp 247-248° C. (decomposed).

$^1$H NMR (CDCl$_3$) δ 2.23 (s, 6H), 2.27 (s, 3H), 3.68 (brs, 2H), 3.98 (s, 3H), 4.15 (s, 2H), 6.50 (dd, J=1.0, 7.5 Hz, 1H), 6.89 (s, 2H), 6.95 (t, J=7.7 Hz, 1H), 7.21 (dd, J=1.0, 8.1 Hz, 1H).

MS Calcd.: 279; MS Found: 280 (M+H).

Reference Example 5

2-[2,6-Dichloro-4-(trifluoromethyl)benzyl]-1-methyl-1H-benzimidazol-7-amine

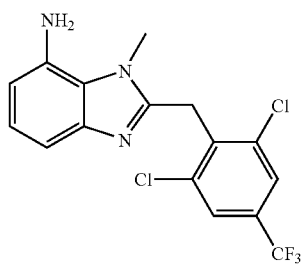

To a solution of [2,6-dichloro-4-(trifluoromethyl)phenyl]acetic acid (273 mg, 1.00 mmol) in toluene (2.0 mL) was added N,N'-carbonyldiimidazole (162 mg, 1.00 mmol) at room temperature. After the reaction mixture was stirred at 50° C. for 15 min, $N^2$-methylbenzene-1,2,3-triamine (137 mg, 1.00 mmol) in toluene (2 mL) was added to the mixture, and the mixture was refluxed for further 60 hr. After the reaction mixture was cooled, the solvent was evaporated in vacuo, and the residue was purified by silica gel column chromatography eluting with 40-60% ethyl acetate/n-hexane gradient mixture to give the title compound (170 mg, 0.455 mmol, 45%) as a colorless solid. The resulting solid was recrystallized from n-hexane/ethyl acetate to give the title compound (137 mg, 0.38 mmol).

mp 240-241° C. (decomposed).

$^1$H NMR (CDCl$_3$) δ 3.71 (brs, 2H), 4.17 (s, 3H), 4.48 (s, 2H), 6.54 (dd, J=0.9, 7.5 Hz, 1H), 6.96 (t, J=7.9 Hz, 1H), 7.19 (dd, J=0.9, 8.1 Hz, 1H), 7.64 (s, 2H)

MS Calcd.: 373; MS Found: 374 (M+H).

Reference Example 6

Methyl 2-(mesitylmethyl)-1-methyl-1H-benzimidazole-7-carboxylate

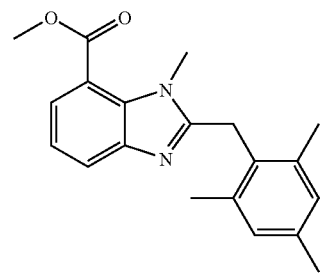

The title compound was prepared from mesityleneacetic acid and methyl 2-(methylamino)-3-nitrobenzoate in the similar method described in Reference Example 5.

mp 164-165° C.

$^1$H NMR (CDCl$_3$) δ 2.23 (s, 6H), 2.29 (s, 3H), 3.92 (s, 3H), 3.97 (s, 3H), 4.19 (s, 2H), 6.91 (s, 2H), 7.18 (t, J=7.8 Hz, 1H), 7.71 (dd, J=1.1, 7.7 Hz, 1H), 7.85 (dd, J=1.1, 8.1 Hz, 1H).

MS Calcd.: 322; MS Found: 0.323 (M+H).

Reference Example 7

Methyl 2-[2,6-dichloro-4-(trifluoromethyl)benzyl]-1-methyl-1H-benzimidazole-7-carboxylate

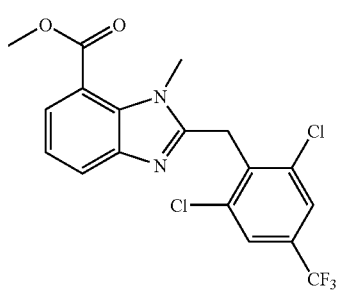

The title compound was prepared from methyl 2-(methylamino)-3-nitrobenzoate in the similar method described in Reference Example 5.

mp 171-172° C.

$^1$H NMR (CDCl$_3$) δ 3.99 (s, 3H), 4.05 (s, 3H), 4.55 (s, 2H), 7.20 (t, J=7.8 Hz, 1H), 7.65 (s, 2H), 7.76 (dd, J=1.1, 7.7 Hz, 1H), 7.83 (dd, J=1.1, 8.1 Hz, 1H).

MS Calcd.: 416; MS Found: 417 (M+H).

Reference Example 8

2-Mesityl-N-[2-(mesitylmethyl)-1-methyl-1H-benzimidazol-7-yl]acetamide

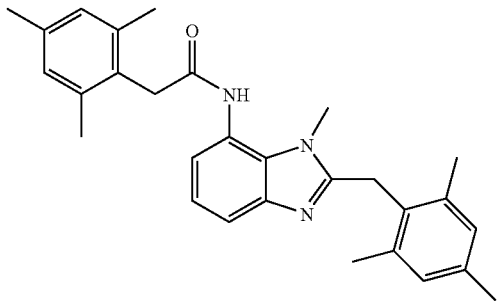

To a solution of mesityleneacetic acid (39 mg, 0.219 mmol) in tetrahydrofuran (0.5 mL) was added N,N'-carbonyldiimidazole (36 mg, 0.219 mmol), and the mixture was stirred at 50° C. for 1 hr. A solution of $N^2$-methylbenzene-1,2,3-triamine (30 mg, 0.219 mmol) in tetrahydrofuran (0.5 mL) was added to the mixture, followed by being stirred at 50° C. for 2 hr and refluxed for 1 hr. Additional mesityleneacetic acid (39 mg, 0.219 mmol) and N,N'-carbonyldiimidazole (36 mg, 0.219 mmol) were added to the mixture, followed by being refluxed for 2 hr. After the reaction mixture was cooled, the solvent was evaporated in vacuo, and the residue was dissolved in 1-methyl-2-pyrrolidinone (0.2 mL). The solution was stirred at 80° C. for 15 hr. The reaction mixture was diluted with water, and ethyl acetate was added thereto. The resulting solid was collected by filtration and washed with water and ethyl acetate. The solid obtained was washed again with diethyl ether to give the title compound (21.1 mg, 0.0480 mmol, 22%) as a solid.

$^1$H NMR (CDCl$_3$+DMSO-d$_6$) δ 2.15 (s, 12H), 2.33 (s, 6H), 3.61 (s, 3H), 3.81 (s, 2H), 4.18 (s, 2H), 6.86 (s, 2H), 6.92 (s, 2H), 7.07-7.13 (m, 2H), 7.53 (d, J=7.8 Hz, 1H), 7.62 (brs, 1H).

Example 1

N,N-Diethyl-2-(mesitylmethyl)-1-methyl-1H-benzimidazol-7-amine

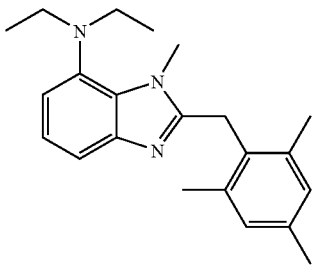

To a solution of 2-(mesitylmethyl)-1-methyl-1H-benzimidazol-7-amine (200 mg, 0.717 mmol), acetaldehyde (0.400 mL, 7.17 mmol) and acetic acid (0.330 mL, 5.78 mmol) in methanol (5.0 mL) was added sodium triacetoxyborohydride (1.52 g, 7.17 mmol) portionwise at 0° C. The mixture was warmed to room temperature and stirred for 14 hr. Saturated aqueous sodium bicarbonate solution (50 mL) was added to the mixture and the mixture was extracted with ethyl acetate (25 mL, three times). Combined organic layers were washed with saturated aqueous sodium bicarbonate solution (20 mL) and brine, dried over anhydrous sodium sulfate and concentrated in vacuo to afford the title compound (237 mg, 0.707 mmol, 97%) as a colorless solid. The resulting solid was recrystallized from n-hexane/ethyl acetate to give the title compound (145 mg, 0.433 mmol).

mp 149-150-151° C. (decomposed).

$^1$H NMR (CDCl$_3$) δ 1.00 (t, J=7.0 Hz, 6H), 2.24 (s, 6H), 2.28 (s, 3H), 3.04-3.16 (m, 4H), 4.10 (s, 3H), 4.15 (s, 2H), 6.90 (s, 2H), 6.99 (dd, J=1.1, 7.9 Hz, 1H), 7.09 (t, J=7.9 Hz, 1H), 7.46 (dd, J=1.1, 7.9 Hz, 1H)

MS Calcd.: 335; MS Found: 336 (M+H).

Example 2

2-[2,6-Dichloro-4-(trifluoromethyl)benzyl]-N,N-diethyl-1-methyl-1H-benzimidazol-7-amine

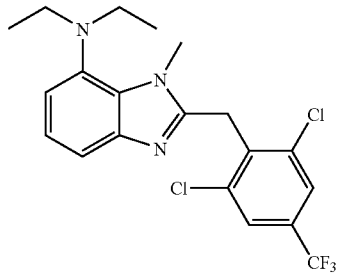

The title compound was prepared from 2-[2,6-dichloro-4-(trifluoromethyl)benzyl]-1-methyl-1H-benzimidazol-7-amine in the similar method described in Example 1.

mp 150-151° C.

$^1$H NMR (CDCl$_3$) δ 1.03 (t, J=7.0 Hz, 6H), 3.04-3.18 (m, 4H), 4.26 (s, 3H), 4.49 (s, 2H), 7.02 (dd, J=1.1, 7.9 Hz, 1H), 7.10 (t, J=7.7 Hz, 1H), 7.44 (dd, J=1.1, 7.9 Hz, 1H), 7.64 (s, 2H).

MS Calcd.: 429; MS Found: 430 (M+H).

Example 3

3-[2-(Mesitylmethyl)-1-methyl-1H-benzimidazol-7-yl]pentan-3-ol

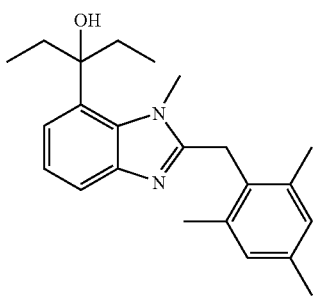

To a solution of methyl 2-(mesitylmethyl)-1-methyl-1H-benzimidazole-7-carboxylate (1.30 g, 4.0 mmol) in tetrahydrofuran (80 mL) was added a solution of ethyllithium in benzene/cyclohexane (90/10) (0.5 M, 32 mL, 16.1 mmol) dropwise at −78° C. The solution was warmed to room temperature over 1 hr followed by addition of saturated aqueous ammonium chloride solution (20 mL). The mixture was extracted with ethyl acetate (100 mL, three times) and the combined organic layers were washed with brine (100 mL), dried over anhydrous sodium sulfate and concentrated in vacuo. The residue was purified by silica gel column chromatography eluting with a 15-25% ethyl acetate/n-hexane gradient mixture to give the title compound (590 mg, 1.68 mmol, 42%) as a colorless solid. The resulting solid was recrystallized from n-hexane/ethyl acetate to give the title compound (435 mg, 1.24 mmol).

¹H NMR (CDCl₃) δ 0.92 (t, J=7.3 Hz, 6H), 1.98 (s, 1H), 2.00-2.16 (m, 4H), 2.23 (s, 6H), 2.29 (s, 3H), 4.16 (s, 2H), 4.19 (s, 3H), 6.91 (s, 2H), 6.98-7.13 (m, 2H), 7.64 (dd, J=1.5, 7.5 Hz, 1H).

MS Calcd.: 350; MS Found: 351 (M+H).

Example 4

7-[1-Ethylprop-1-en-1-yl]-2-(mesitylmethyl)-1-methyl-1H-benzimidazole

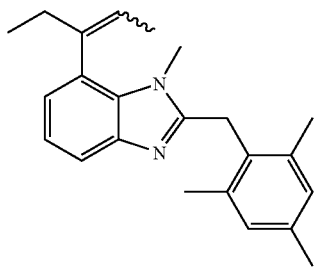

A solution of 3-[2-(mesitylmethyl)-1-methyl-1H-benzimidazol-7-yl]pentan-3-ol (200 mg, 0.571 mmol) and p-toluenesulfonic acid monohydrate (326 mg, 1.71 mmol) in xylene (10 mL) was refluxed for 3 hr. After cooling, the mixture was diluted with ethyl acetate (50 mL) and washed with saturated aqueous sodium bicarbonate solution (30 mL) and brine (30 mL). The organic layer was dried over anhydrous sodium sulfate and concentrated in vacuo. The residue was purified by silica gel column chromatography eluting with 10-20% ethyl acetate/n-hexane gradient mixture to give the title compound (180 mg, 0.542 mmol, 95%, as a mixture of geometric isomers) as a colorless solid.

¹H NMR (CDCl₃) δ 0.96 (t, J=7.3 Hz, 2.4H), 1.05 (t, J=7.3 Hz, 0.6H), 1.37-1.44 (m, 0.6H), 1.82 (d, J=6.8 Hz, 2.4H), 2.22-2.45 (m, 2H), 2.23 (s, 6H), 2.28 (s, 3H), 3.70 (s, 0.6H), 3.71 (s, 2.4H), 4.16 (s, 1.6H), 4.17 (s, 0.4H), 5.51 (q, J=7.0 Hz, 0.8H), 5.65-5.78 (m, 0.2H), 6.81 (dd, J=1.1, 7.2 Hz, 0.2H), 6.85-6.89 (m, 0.8H), 6.90 (s, 2H), 7.04-7.18 (m, 1H), 7.56-7.62 (m, 1H).

MS Calcd.: 332; MS Found: 333 (M+H).

Example 5

7-(1-Ethylpropyl)-2-(mesitylmethyl)-1-methyl-1H-benzimidazole

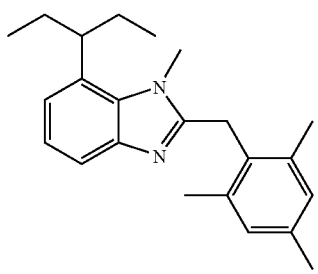

To a solution of 7-[1-ethylprop-1-en-1-yl]-2-(mesitylmethyl)-1-methyl-1H-benzimidazole (110 mg, 0.331 mmol) in tetrahydrofuran (3.5 mL) was added a solution of borane-dimethyl sulfide complex in tetrahydrofuran (1.9 M, 3.5 mL, 6.63 mmol) at 0° C. After the reaction mixture was stirred at room temperature for 15 hr, acetic acid (5.0 mL) was added to the mixture and the mixture was heated at 120° C. for 2 hr.

After the reaction mixture was cooled, the mixture was poured into saturated aqueous sodium bicarbonate solution (50 mL) and extracted with ethyl acetate (50 mL, twice). The combined organic layer was washed with brine, dried over anhydrous sodium sulfate and concentrated in vacuo. The residue was purified by silica gel column chromatography eluting with 10-25% ethyl acetate/n-hexane gradient mixture to give the title compound (12 mg, 0.0359 mmol, 11%) as a colorless solid.

¹H NMR (CDCl₃) δ 0.84 (t, J=7.4 Hz, 6H), 1.66-1.87 (m, 4H), 2.23. (s, 6H), 2.29 (s, 3H), 3.22-3.41 (m, 1H), 3.90 (s, 3H), 4.19 (s, 2H), 6.90 (s, 2H), 7.02-7.07 (m, 1H), 7.14 (t, J=7.8 Hz, 1H), 7.52 (dd, J=1.2, 7.8 Hz, 1H).

MS Calcd.: 334; MS Found: 335 (M+H).

Example 6

3-{2-[2,6-Dichloro-4-(trifluoromethyl)benzyl]-1-methyl-1H-benzimidazol-7-yl}pentan-3-ol

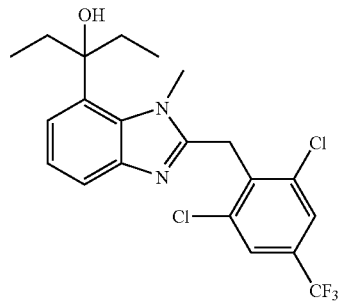

The title compound was prepared from methyl 2-[2,6-dichloro-4-(trifluoromethyl)benzyl]-1-methyl-1H-benzimidazole-7-carboxylate in the similar method described in Example 3.

¹H NMR (CDCl₃) δ 0.93 (t, J=7.5 Hz, 6H), 2.02 (s, 1H), 2.02-2.20 (m, 4H), 4.31 (s, 3H), 4.52 (s, 2H), 7.01-7.15 (m, 2H), 7.60 (dd, J=1.5, 7.5 Hz, 1H), 7.65 (s, 2H).

MS Calcd.: 444; MS Found: 445 (M+H).

Example 7

2-[2,6-Dichloro-4-(trifluoromethyl)benzyl]-7-[1-ethylprop-1-en-1-yl]-1-methyl-1H-benzimidazole

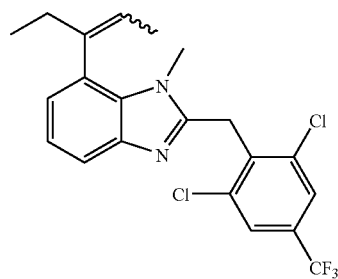

The title compound was prepared from 3-{2-[2,6-dichloro-4-(trifluoromethyl)benzyl]-1-methyl-1H-benzimidazol-7-yl}pentan-3-ol in the similar method described in Example 4.

¹H NMR (CDCl₃) δ 0.98 (t, J=7.5 Hz, 2.4H), 1.08 (t, J=7.3 Hz, 0.6H), 1.35-1.49 (m, 0.6H), 1.86 (d, J=6.8 Hz, 2.4H), 2.17-2.56 (m, 2H), 3.88 (s, 3H), 4.49 (s, 1.6H), 4.50 (s, 0.4H), 5.55 (q, J=6.8 Hz, 0.8H), 5.76 (q, J=6.5 Hz, 0.2H), 6.84 (dd, J=0.9, 7.3 Hz, 0.2H), 6.90 (dd, J=1.1, 7.2 Hz, 0.8H), 7.06-7.21 (m, 1H), 7.53-7.61 (m, 1H), 7.64 (s, 2H).

MS Calcd.: 426; MS Found: 427 (M+H).

Example 8

2-{2-[2,6-Dichloro-4-(trifluoromethyl)benzyl]-1-methyl-1H-benzimidazol-7-yl}-1-methylbutyl acetate

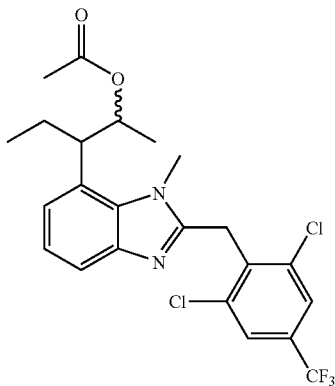

Example 9

3-{2-[2,6-Dichloro-4-(trifluoromethyl)benzyl]-1-methyl-1H-benzimidazol-7-yl}pentan-2-ol

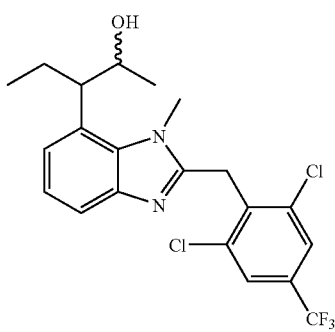

To a solution of 2-[2,6-dichloro-4-(trifluoromethyl)benzyl]-7-[1-ethylprop-1-en-1-yl]-1-methyl-1H-benzimidazole (60 mg, 0.141 mmol) in tetrahydrofuran (1.5 mL) was added a solution of borane-dimethyl sulfide complex in tetrahydrofuran (1.9 M, 1.5 mL, 2.81 mmol) at 0° C. After the reaction mixture was stirred at room temperature for 15 hr, acetic acid (3.0 mL) was added thereto and the mixture was heated at 120° C. for 2 hr. After cooling, the mixture was poured into saturated aqueous sodium bicarbonate solution (50 mL) and extracted with ethyl acetate (50 mL, twice). The combined organic layer was washed with brine, dried over anhydrous sodium sulfate and concentrated in vacuo. The residue was purified by silica gel column chromatography eluting with 5-50% ethyl acetate/n-hexane gradient mixture to give 2-{2-[2,6-dichloro-4-(trifluoromethyl)benzyl]-1-methyl-1H-benzimidazol-7-yl}-1-methylbutyl acetate (17 mg, 0.0349 mmol, 25%) and 3-{2-[2,6-dichloro-4-(trifluoromethyl)benzyl]-1-methyl-1H-benzimidazol-7-yl}pentan-2-ol (less polar diastereomer; 2.4 mg, 0.00539 mmol, 4%, more polar diastereomer; 2.5 mg, 0.00562 mmol, 4%).

Example 8

2-{2-[2,6-Dichloro-4-(trifluoromethyl)benzyl]-1-methyl-1H-benzimidazol-7-yl}-1-methylbutyl acetate (as a mixture of diastereomers)

$^1$H NMR (CDCl$_3$) δ 0.75-0.91 (m, 3H), 1.07 (d, J=6.0 Hz, 1.5H), 1.27 (d, J=6.4 Hz, 1.5H), 1.64-2.04 (m, 2H), 1.81 (s, 1.5H), 2.08 (s, 1.5H), 3.55-3.75 (m, 1H), 4.08 (s, 1.5H), 4.11 (s, 1.5H), 4.53 (s, 2H), 5.12-5.31 (m, 1H), 7.04-7.23 (m, 2H), 7.49-7.59 (m, 1H), 7.65 (s, 2H).

MS Calcd.: 486; MS Found: 487 (M+H).

Example 9

3-{2-[2,6-Dichloro-4-(trifluoromethyl)benzyl]-1-methyl-1H-benzimidazol-7-yl}pentan-2-ol (Less polar diastereomer) $^1$H NMR (CDCl$_3$) δ 0.81 (t, J=7.3 Hz, 3H), 1.36 (d, J=6.0 Hz, 3H), 1.50 (d, J=3.0 Hz, 1H), 1.68-1.97 (m, 2H), 3.37-3.51 (m, 1H), 3.94-4.03 (m, 1H), 4.10 (s, 3H), 4.52 (s, 2H), 7.11-7.24 (m, 2H), 7.56 (dd, J=1.5, 7.5 Hz, 1H), 7.65 (s, 2H)

(More polar diastereomer) $^1$H NMR (CDCl$_3$) δ 0.86 (t, J=7.3 Hz, 3H), 1.12 (d, J=6.4 Hz, 3H), 1.45 (d, J=6.0 Hz, 1H), 1.74-2.11 (m, 2H), 3.52-3.66 (m, 1H), 4.00-4.17 (m, 1H), 4.12 (s, 3H), 4.52 (s, 2H), 7.05 (d, J=7.5 Hz, 1H), 7.17 (t, J=7.9 Hz, 1H), 7.55 (d, J=7.9 Hz, 1H), 7.65 (s, 2H)

MS Calcd.: 444; MS Found: 445 (M+H).

Example 10

[7-(1-Ethylpropyl)-1-methyl-1H-benzimidazol-2-yl](mesityl)methanol

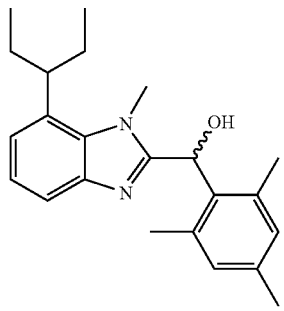

A solution of n-butyllithium in n-hexane (1.6M solution, 0.25 mL, 0.40 mmol) was added dropwise to a solution of 2-bromo-7-(1-ethylpropyl)-1-methyl-1H-benzimidazole (100 mg, 0.36 mmol) in diethyl ether (4 mL) at 0° C. To the reaction mixture was added a solution of mesitaldehyde (74 mg, 0.50 mmol) in diethyl ether (1 mL) at 0° C. The reaction mixture was stirred for 0.5 hr, and the reaction was quenched by the addition of 1N hydrochloric acid to the mixture, and the mixture was extracted with ethyl acetate. The organics were dried over anhydrous magnesium sulfate, filtered, and concentrated in vacuo. The residue was purified by preparative HPLC eluting with a 10-100% water/acetonitrile gradient mixture containing 0.1% trifluoroacetic acid. The fractions containing the title compound were concentrated in vacuo, and the residue was diluted with ethyl acetate and washed with saturated aqueous sodium hydrogen carbonate solution. The organics were dried over anhydrous magnesium sulfate, filtered, and concentrated in vacuo. The resulting solid was recrystallized from ethanol/water to give the title compound (20 mg, 0.057 mmol, 16%) as colorless crystals.

mp 132-134° C.

$^1$H NMR (CDCl$_3$) δ 0.74 (t, J=7.2 Hz, 3H), 0.82 (t, J=7.2 Hz, 3H), 1.60-1.78 (m, 4H), 2.19 (s, 6H), 2.27 (s, 3H), 3.12-3.22 (m, 1H), 3.48 (s, 3H), 4.89 (s, 1H), 6.22 (s, 1H), 6.85 (s, 2H), 7.09 (d, J=7.5 Hz, 1H), 7.24 (t, J=7.5 Hz, 1H), 7.58 (d, J=7.5 Hz, 1H).

MS Calcd.: 350; MS Found: 351 (M+H).

Experiment 1

Measurement of CRF Binding Inhibitory Rate

A receptor binding experiment was carried out using a human CRF receptor expressing CHO cellular membrane fraction and ovine CRF, [$^{125}$I]-tyr$^0$($^{125}$I-CRF). 1000 nM of a test compound was incubated with 1 μg of human CRF receptor expressing CHO cellular membrane fraction and 50 pM of $^{125}$I-CRF in a binding assay buffer (50 mM Tris-HCl, 5 mM EDTA, 10 mM MgCl$_2$, 0.05% CHAPS, 0.1% BSA, 0.5 mM PMSF, 0.1 μg/mL pepstatin, 20 μg/mL leupeptin, pH 7.5). In addition, for measuring nonspecific binding (NSB), 0.1 μM unlabelled human Urocortin was incubated with 5 μg of human CRF receptor expressing CHO cellular membrane fraction and 50 pM of $^{125}$I-CRF in a binding assay buffer. After a binding reaction was carried out at room temperature for 1.5 hr, the membrane was entrapped on a glass filter (UniFilter plate GF-C/Perkin Elmer) by suction filtration using a cell harvester (Perkin Elmer), and washed with ice-cooled 50 mM Tris-HCl (pH 7.5). After drying the glass filter, a liquid scintillation cocktail (Microscinti 0, Perkin Elmer) was added, and the radioactivity of $^{125}$I-CRF remaining on a glass filter was measured using Topcount (Perkin Elmer).

(TB-SB)/(TB-NSB)×100 (SB: radioactivity when a compound is added, TB: maximum binding radioactivity, NSB: nonspecific binding radioactivity) were calculated to obtain binding inhibitory rates under the range of the presence from 0.05 nM to 10 μM of each compound. The IC$_{50}$ values were calculated by using GraphPad Prism software. The compounds of Experimental Examples 1, 2, 3, 4, 5, 6, 7, 8, 9 and 10 have been tested in this assay and found to exhibit IC$_{50}$ values of less than 1 μM.

Preparation Example 1

| | |
|---|---:|
| (1) Compound of Example 1 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Carboxymethylcellulose calcium | 20 mg |
| Total | 120 mg |

According to a conventional method, the above (1) to (6) are mixed and compressed into a tablet with a tableting machine.

INDUSTRIAL APPLICABILITY

Compound (I) of the present invention has an excellent CRF antagonistic activity, etc. and therefore useful as pharmaceuticals for treating or preventing affective disorder, depression, anxiety, and the like.

The invention claimed is:

1. A compound represented by the formula (I):

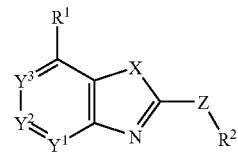

wherein R$^1$ is an amino substituted with one or two C$_{1-4}$ alkyl;
R$^2$ is 2,4,6-trisubstituted phenyl;
X is —NR$^3$— wherein R$^3$ is C$_{1-6}$ alkyl;
Y$^1$, Y$^2$ and Y$^3$ are methines; and
Z is a methylene;
or a salt thereof.

2. The compound according to claim 1 wherein R$^1$ is an amino substituted with two C$_{1-4}$ alkyls.

3. The compound according to claim 1 wherein R$^2$ is 2,4,6-trisubstituted phenyl.

4. The compound according to claim 1 wherein X is —NR$^3$—.

5. The compound according to claim 1 wherein Y$^1$, Y$^2$ and Y$^3$ are methines.

6. The compound according to claim 1 wherein Z is a methylene.

7. The compound according to claim 1 wherein R$^1$ is di-C$_{1-4}$ alkylamino;
R$^2$ is 2,4,6-trisubstituted phenyl, wherein the substituent is selected from the group consisting of (1) halogen atom and (2) optionally halogenated C$_{1-4}$ alkyl;
X is —N(C$_{1-6}$ alkyl)-;
Y$^1$ is methine;
Y$^2$ is methine;
Y$^3$ is methine; and
Z is a methylene.

8. (1) N,N-diethyl-2-(mesitylmethyl)-1-methyl-1H-benzimidazol-7-amine; and
(2) 2-[2,6-dichloro-4-(trifluoromethyl)benzyl]-N,N-diethyl-1-methyl-1H-benzimidazol-7-amine;
or a salt thereof.

9. A pharmaceutical which comprises the compound according to claim 1 and a pharmaceutically acceptable carrier.

10. A method for treating affective disorder, depression, anxiety or irritable bowel syndrome comprising administering an effective amount of a compound according to claim 1 or a salt thereof to a patient in need thereof.

* * * * *